United States Patent
Lopez et al.

(10) Patent No.: US 7,427,401 B2
(45) Date of Patent: Sep. 23, 2008

(54) METHOD OF MODULATING LEUKEMIC CELL AND EOSINPHIL ACTIVITY WITH MONOCLONAL ANTIBODIES

(75) Inventors: Angel Lopez, Medindie (AU); Richard D'Andrea, Stonybell (AU)

(73) Assignee: Medvet Science Pty Ltd., South Australia (AU)

( * ) Notice: Subject to any disclaimer, the term of this patent is extended or adjusted under 35 U.S.C. 154(b) by 191 days.

(21) Appl. No.: 10/774,887

(22) Filed: Feb. 9, 2004

(65) Prior Publication Data
US 2004/0265957 A1 Dec. 30, 2004

Related U.S. Application Data

(62) Division of application No. 09/762,963, filed as application No. PCT/AU99/00659 on Aug. 13, 1998, now Pat. No. 6,720,155.

(30) Foreign Application Priority Data
Aug. 13, 1998 (AU) ............................ PP5251

(51) Int. Cl.
 *A61K 39/395* (2006.01)
(52) U.S. Cl. ............... 424/141.1; 424/143.1; 424/144.1
(58) Field of Classification Search ................ None
See application file for complete search history.

(56) References Cited

FOREIGN PATENT DOCUMENTS

WO WO 97/28190 8/1997

OTHER PUBLICATIONS

Menzies-Gow A, Robinson DS. 2002, Curr Opin Pulm Med. vol. 8(1):33-38. Eosinophils, eosinophilic cytokines (IL-5), and anti-eosinophilic therapy in asthma.*
Canhao et al. (2000) J. Rheumatol., 27(4):1102-1103.*
Fox et al. (1997), Curr Opin Rheumatol, 9(5):393-399.*
Molina et al. (1996), 60(6):699.*
Beers and Berkow, The Merck Manual of diagnosis and therapy. 17th edition, (1999), pp. 944-955.*
Bagley, C.J., et al. Blood 1997 vol. 89 (5) pp. 1471-1482.
Sun, Q. et al. Blood, 1996 vol. 88 (10) Suppl. 1 Abstract 2170 p. 545a.
Stomski et al. "Human Interleukin-3 (IL-3) Induces Disulfide-Linked IL-3 Receptor α- and β-Chain Heterodimerization, Which is Required for Receptor Activation but Not High-Affinity Binding", *Molecular and Cellular Biology*, 16(6): p. 3035-3046, 1996.
Woodcock et al. The Human Granulocyte-Macrophage Colony-Stimulating Factor (GM-CSF) Receptor Exists as a Preformed and Receptor Complex That Can Be Activated by GM-CSF, Interleukin-3, or Interleukin-5', *Blood*, 90(8): p. 3005-3017, 1997.
Watanabe et al. "Monoclonal Antibody Against the Common β Subunit ($β_c$) of the Human Interleukin-3 (IL-3), IL-5, and Granulocyte-Macrophage Colony-Stimulating Factor Receptors Shows Upregulation of $β_c$ by IL-1 and Tumor Necrosis Factor-α", *Blood*, 80(9): p. 2215-2220, 1992.
"Granulocyte-Macrophage Colony-Stimulating Factor Mimicry and Receptor Interactions", *Immunol. Res.*, 13: p. 96-109, 1994.

* cited by examiner

*Primary Examiner*—Prema Mertz
(74) *Attorney, Agent, or Firm*—Foley & Lardner LLP

(57) ABSTRACT

A method of isolating a monoclonal antibody capable of inhibiting any one of IL-3, GM-CSF and IL-5 binding to the common receptor $β_c$, or a monoclonal antibody capable of inhibiting the cytokines binding to a receptor analogous to $β_c$. The method includes the steps of immunizing an animal with a cytokine receptor or portion of a cytokine containing the critical binding site which portion includes the extracellular domain 4 or analogous domain in the analogous common receptor or part thereof. Antibodies producing cells from the animal are then isolated and fused with a myeloma cell line and then screened for a cell line that produces an antibody of the desired type. A monoclonal antibody, or fragments thereof capable of inhibiting the binding of the cytokines IL-3, GM-CSF and IL-5 to the $β_c$ receptor, and a hybridoma cell line producing the antibody are also claimed.

2 Claims, 14 Drawing Sheets

A)

B)

METHOD OF MODULATING LEUKEMIC CELL AND EOSINPHIL ACTIVITY WITH MONOCLONAL ANTIBODIES

CROSS REFERENCE TO RELATED APPLICATIONS

This application is a divisional of U.S. application Ser. No. 09/762,963 filed Feb. 14, 2001, now U.S. Pat. No. 6,720,155 which is a 35 U.S.C § 317 of a PCT/AU99/00659, which claims priority from Australia PP5251, filed Aug. 13, 1998. The entire disclosure and contents of the above patents and applications are hereby incoporated by reference.

FIELD OF THE INVENTION

This invention relates to a method of isolating monoclonal antibody inhibitors and reagents derived therefrom and other inhibitors of cytokine binding including monoclonal antibodies and reagents derived therefrom and small molecules capable of inhibiting binding of GM-CSF, IL-3 and IL-5 to the common beta receptor subunit.

INTRODUCTION

Human interleukin (IL)-5, IL-3 and granulocyte-macrophage colony-stimulating factor (GM-CSF) are cytokines involved in hemopoiesis and inflammation (Metcalf; 1986). All three cytokines stimulate eosinophil production, function and survival (Metcalf; 1986) and therefore have the ability to influence inflammatory diseases such as asthma, atopic dermatitis and allergic rhinitis where the eosinophil plays a major effector role. IL-5, being the eosinophil specific cytokine, has received most of the initial attention with IL-5 mRNA and protein levels noted to be elevated in lung tissue and bronchoalveolar lavage (BAL) fluid from symptomatic asthma patients (Fukuda et al 1994). Correlation between IL-5 levels and allergen challenge and disease activity have also been seen (Sur et al, 1996). It is becoming apparent, however, that not only IL-5 but also GM-CSF and IL-3 play a role in eosinophil production and activation in asthma as there is evidence of both GM-CSF and IL-3 being synthesized at sites of allergic inflammation (Bagley et al, 1997b; Allen et al 1997). It is possible that expression of these cytokines contributes to the total number of infiltrating eosinophils and the degree of eosinophil activation. Alternatively, they may be responsible for different phases of eosinophil infiltration. Recent kinetic data from patients undergoing antigen challenge showed that IL-5 levels increased between days 2-7 post challenge, whilst GM-CSF peaked at day 2, and remained elevated throughout day 16. Furthermore, GM-CSF detection extended beyond the site of allergen challenge.

IL-S, GM-CSF and IL-3 stimulate eosinophils and other normal and cancer cells by binding to cell surface receptors that comprise a ligand-specific α chain and a β chain which is shared by the three receptors ($β_c$) (Bagley et al 1997a). Binding to each receptor α chain is the initial step in receptor activation, however, engagement of either α chain alone is not sufficient for activation to occur. Recruitment of $β_c$ by each ligand: α chain complex follows, a step that has two major functional consequences: firstly, it allows the binding of IL-5, GM-CSF and IL-3 to become essentially irreversible; and secondly, it leads to full receptor activation (Bagley et al 1997a). Since $β_c$ is the major signalling component of these receptors its engagement leads to the activation of JAK-2, STAT-5 and other signalling molecules culminating in the full plethora of cellular activities commonly associated with either IL-5, GM-CSF and IL-3 stimulation such as eosinophil adherence, priming for degranulation and cytotoxicity, and prolongation of viability (Bates et al, 1996).

In order to block or antagonize the activity of eosinophil-activating cytokines in vivo three major approaches are being tried. One of them utilizes antibodies to the implicated cytokines. For example, antibodies to IL-5 are being used in an animal model of allergen-induced asthma and have shown to have a relatively long lasting effect in preventing eosinophil influx into the airways and bronchial hyperresponsiveness (Mauser et al, 1995). A second approach relies on IL-5 or GM-CSF mutants which can bind to the respective α chains with wild type affinity but which have lost or shown reduced ability to interact with human $β_c$. IL-5 mutants such as E13Q, E13K and E13R, and the human GM-CSF mutant E21R directly antagonize the functional activation of eosinophils by IL-5 or GM-CSF respectively (Tavernier et al 1995; McKinnon et al 1997; Hercus et al 1994b). However, at least in the case of E13K, eosinophil survival is not antagonized and in fact this mutant is able to support eosinophil survival (McKinnon et al 1997). A third approach involves the use of soluble receptor α chains which can sequester circulating cytokines. However, this carries the risk of a cytokine:receptor α chain complex potentially interacting with surface-expressed $β_c$ and triggering receptor activation. The common theme amongst these approaches is that they tackle a single receptor system involving either IL-5, GM-CSF or IL-3 leaving the other two eosinophil-acting cytokines unaffected. Although the concomitant administration of IL-5 and GM-CSF antagonists may be considered, this may be clinically impracticable.

An alternative approach to blocking eosinophil-activating cytokines involves targeting the common β chain of their receptors. Although $β_c$ does not directly bind IL-5, GM-CSF or IL-3 alone, it does bind to these cytokines complexed to the appropriate receptor α chain. Lopez et al in WO 97/28190, which is incorporated herein by reference in its entirety, have identified the major binding sites of, $β_c$ for the IL-5:IL-5Rα, GM-CSF:GM-CSFRα and IL-3:IL-3Rα complexes. Significantly, these sites are utilized by all three complexes and comprise the predicted B'-C' loop and F'-G' loop in $β_c$. Thus targeting $β_c$ is not only desirable but also feasible, with the added potential to allow the simultaneous inhibition of IL-5, GM-CSF and IL-3 action by a single agent. These workers have shown that certain mutants in the B'-C' and the F'-G' loop fail to bind IL-5, GM-CSF and IL-3.

SUMMARY OF THE INVENTION

The present invention results from the isolation of a monoclonal antibody BION-1) raised against the membrane proximal domain (domain 4) of $β_c$ which is able to block the production and activation of human eosinophils stimulated by IL-5, GM-CSF or IL-3 and blocks the growth of leukaemic cell lines. This MoAb was able to block the high affinity binding of all three cytokines to eosinophils by binding to residues in the predicted B'-C' and F'-G' loops of $β_c$, and prevented receptor dimerization and $β_c$ phosphorylation. It was found that raising an antibody capable of blocking the binding of all three cytokines was possible by screening monoclonal antibody-expressing hybridoma cell lines arising from immunising mice with cells expressing only domain 4 of $β_c$ and lacking domains 1 to 3 and expressing domain 4 and the transmembrane and cytoplasmic regions.

Additionally this finding is likely to have implications for other members of the cytokine receptor superfamily some of which are shared subunits in a given subfamily (that is they bind several cytokines), and some which are ligand specific and bind to only one cytokine. The receptor α-chains for GM-CSF, IL-3 and IL-5 and $\beta_c$ belong to the rapidly expanding cytokine receptor superfamily. Within this superfamily several sub-families are now emerging that are characterized by the sharing of a communal receptor subunit by multiple ligands: gp 130 acts as an affinity converter and signal transducer for IL-6 (Hibi et al., 1990; Taga et al., 1992), IL-11 (Hilton et al., 1994), oncostatin M (Liu et al., 1992), ciliary neurotrophic factor, leukaemia inhibitory factor (LIF) (Ip et al., 1992) and cardiotrophin-1(Pennica et al., 1995); the LIF receptor (LIFR) also binds ciliary neurotrophic factor (Davis et al., 1993), cardiotrophin-1 (Pennica et al., 1995) and oncostatin M in addition to LIF (Gearing et al., 1994); IL-2R β supports affinity conversion and signalling of IL-2 and IL-15 (Giri et al., 1994); IL-2R γ chain affinity converts IL-2 (Takeshita et al., 1992), IL-4 (Russell et al., 1993), IL-7 (Noguchi et al., 1993), IL-9 (Kimura et al., 1995) and IL-15 (Giri et al., 1994); evidence also suggests that IL-4 and IL-13 share a receptor component (Zurawski et al., 1993) and this subunit has recently been cloned (Hilton et al., 1996). It is not known which residues in gp 130, LIFR and IL-2R β and γ chains are important for ligand binding or indeed whether different ligands share or have unique sets of binding determinants on these communal receptor subunits. Because these common subunits are vital for transducing signals by several ligands, the possibility arises that interfering with the ability of these common subunits to bind ligand or to form homodimers may affect the action of more than one ligand.

Clear similarities in structure between $\beta_c$ and other cytokine receptors have been recognised and similarities in at least part of the binding site, the F'-G' loop, have been identified in Lopez et al in WO 97/28190. Accordingly it is an expectation that the means employed by the inventors to obtain a monoclonal antibody that inhibits binding of IL-3, GM-CSF and IL-5 will also lead to the isolation of monoclonal antibodies that inhibit binding of other cytokines to their respective receptors.

In a broad form of a first aspect the invention could be said to reside in a method of isolating a monoclonal antibody capable of inhibiting any one of IL-3, GM-CSF and IL-5 binding to the common receptor $\beta_c$, or a monoclonal antibody capable of inhibiting a cytokines binding to a receptor analogous to $\beta_c$, said method comprising the step of immunising an animal with a cytokine receptor or portion of a cytokine receptor containing the critical binding site which portion might include the extracellular domain 4 or analogous domain in the analogous common receptor or part thereof, isolating antibody producing cells from said animal and fusing antibody producing cells with a myeloma cell line, screening for a cell line that produces an antibody of the desired type.

The immunisation may involve introducing a cDNA clone of a portion of or all of the common receptor including the extracellular domain 4 or analogous domain in the analogous common receptor or part thereof, into a cell and proliferating said cells to form a recombinant cell line, inoculating an animal with said recombinant cell line, isolating antibody producing cells from said animal and fusing the antibody producing cell line with a myeloma cell line to form a hybridoma cell line, screening for a hybridoma cell line that produces an antibody that binds to the recombinant cell line but not to the parent, and then testing for inhibition against all three cytokines. In one form the cell into which the cDNA clone is introduced is mammalian and one commonly used mammalian cell line is a COS cell.

The cDNA may encode a full or partial portion of domain 4 when it is in a configuration where the F'-G' loop and/or the B'-C' loop is in its native shape. The data below show that cDNA encoding substantially only domain 4 of the extracellular portion of $\beta_c$ as well as the transmembrane and the intracellular portions maintains these sites in a sufficiently integral conformation so that an antibody raised thereagainst will give the inhibition sought. It is postulated that the same will be the case for analogous receptors for the cytokine superfamily. This method should be distinguished from immunising with the whole receptor since the extracellular domain 4 is likely to be covered or masked by other domains in the whole receptor.

$\beta_c$ has two repeats of the cytokine receptor module (CRM), each of which has two discrete folding domains (CRDs), so that in total $\beta_c$ has 4 domains hence named domains 1 to 4 (β1 to 4). It is postulated that domain 2 of any CRM may be an equivalent of domain 4 and therefore domain 2 may be used in the immunisation.

In addition the domain 4 of $\beta_c$ or equivalent domain in other cytokine receptors may be expressed in isolation in a microbial host such as *Escherichia coli* and used to immunise animals for developing monoclonal antibodies.

The analogous receptor may be any one of the cytokine superfamily receptors but not limited to the group comprising $\beta_c$, LIFR, gp130, IL-2Rβ, IL-4R/IL-13R, IL-2Rγ, IL-3Rα, EPOR, TPOR and OBR.

It will be understood that in one specific form of this aspect of the invention the method is used to isolate a monoclonal antibody that inhibits cytokine binding to a common receptor subunit. The common receptor is envisaged to be selected from the group of receptors acting for more than one cytokine including but not limited to gp130, LIFR, IL2Rβ/IL2Rα, and EL-4R/IL-13R in addition to $\beta_c$.

It will also be understood that the invention encompasses monoclonal antibodies or fragments thereof produced as a result of this first form of the invention.

In a broad form of a second aspect the invention could be said to reside in a monoclonal antibody, or fragments thereof capable of inhibiting the binding of the three cytokines IL-3, GM-CSF and IL-5 to the $\beta_c$ receptor.

The degree of inhibition may range from complete inhibition to moderate inhibition, which inhibition will of course be dependent on the amount of monoclonal antibody or fragments thereof added to inhibit and the relative affinity of the antibody or fragment thereof to the $\beta_c$.

The extent of inhibition of respective ones of the three cytokines is not necessarily identical and may vary, so the different cytokines may be inhibited from binding to different degrees.

The antibody fragments may be larger portions such as Fab fragments or much smaller fragments of the variable region. These fragments may be used as separate molecules or alternatively may form part of a recombinant molecule which is then used for therapeutic purposes. Thus for example the monoclonal antibody may be "humanised" by recombining nucleic acid encoding the variable region of the monoclonal antibody with nucleic acid encoding non-variable regions of human origin in an appropriate expression vector.

The inhibition preferably leads to blocking of at least one function of all three cytokines. One of the benefits that is proposed to be derived from these antibodies or antibody fragments is their use in modifying cells stimulated by one of the three cytokines, and more in one specific form modifying the activity of the three cytokines is proposed to impact greatly on eosinophil function. Therefore preferably the activity leads to inhibition of stimulation of effector cell activation and where the antibody or fragment thereof is to be used for treatment of asthma leads most preferably to inhibition of IL-5, IL-3 & GM-CSF mediated eosinophil activation. It will be understood however that cells other than eosinophils are also the effectors of adverse conditions in humans and animals as a result of stimulation by these cytokines and inhibition of such stimulation is also contemplated by this invention. These include cells that express either one or all of GM-CSF, IL-3 and IL-5 receptors, the stimulation of which leads to pathology. Examples of these are leukaemic cells, endothelial cells, breast cancer cells, prostate cancer cells, small cell lung carcinoma cells, colon cancer cells, macrophages in chronic inflammation such as rheumatoid arthritis, dendritic cells for immunosuppression and neutrophils in inflammation.

Thus in one form the invention may be said to reside in an inhibitor of leukaemic cell growth wherein the inhibitor is capable of inhibiting the binding of one or all of IL-3, GM-CSF and IL-5 to the $\beta_c$ receptor. The inhibitor may be BION-1 or an agent capable of inhibiting BION-1 binding with $\beta_c$.

A number of different facets of eosinophil function might be modified so that in one form IL-5, IL-3 & GM-CSF mediated eosinophil survival is inhibited or blocked. In a second form IL-5, IL-3 and GM-CSF mediated eosinophil activation is inhibited or blocked.

In one form of this second aspect of the invention the monoclonal antibody or fragment thereof binds to at least the F'-G' loop of domain 4 of the $\beta_c$ subunit.

In an alternative form the monoclonal antibody or fragment thereof binds to at least the B'-C' loop of domain 4 of the $\beta_c$ subunit but this alternative form is not limited to monoclonal antibodies or fragments thereof that only bind to the F'-G' loop but includes monoclonal antibodies or fragments thereof that perhaps binds to both the F'-G' as well as the B'-C' loop of domain 4 of the $\beta_c$.

It is thought that the monoclonal antibody isolated by the inventors inhibits dimerisation of the common receptor units and thus the invention might encompass an antibody or fragments thereof of the second aspect of the invention that inhibit $\beta_c$ receptor dimerisation.

In one very specific form the monoclonal antibody is the antibody produced by the hybridoma cell line BION-1 (ATCC HB-12525).

In a broad form of a third aspect the invention could be said to reside in a hybridoma cell line capable of producing a monoclonal antibody of any form of the first or second aspect of the invention.

In one specific form of the third aspect of the invention the hybridoma cell line is BION-1 (ATCC HB-12525).

Since GM-CSF, IL-3 and IL-5 need to bind their respective a chains before being able to interact with $\beta_c$, at present most screening for new inhibitors utilise cell-based assays where both, α and $\beta_c$ receptor units are co-expressed. Solid phase assays rely on inhibition of GM-CSF, IL-3 or IL-5 to their respective a chain only since these cytokines cannot bind to $\beta_c$ alone. Since BION-1, unlike these three cytokines, can directly bind to $\beta_c$ we propose that it can be used as a novel solid phase screening assay. Any compound that binds the appropriate site which is likely to inhibit all three cytokines will also inhibit the binding of BION-1. Additionally once further inhibitory compounds are uncovered these could be used in the place of BION-1 in that screening process. This therefore facilitates the screening of larger number of candidate inhibitor compounds.

In a broad form of a fourth aspect therefore the invention could be said to reside in a method of screening peptides, oligonucleotides and other small molecules for their capacity to competitively inhibit the binding of BION-1 or the binding of an agent capable of inhibiting BION-1 binding, to the $\beta_c$ subunit.

Generally the screening assay involves contacting BION-1 or fragment thereof with the $\beta_c$ subunit or fragment thereof as well as a candidate inhibitory compound, and measuring the degree of binding.

A reporting means is preferably provided to facilitate the detection of binding of BION1 or fragment thereof with $\beta_c$ subunit or fragment thereof. Thus, for example, a competitive binding assay using labelled BION-1 could be used for this purpose. $\beta_c$ or domain 4 of $\beta_c$ is immobilized on a plate or tube and several compounds added, followed by labelled or tagged BION-1 or fragments thereof. Since BION-1 binds the region of $\beta_c$ involved in binding all three cytokines, any compounds that block or reduce the binding of BION-1 or fragments thereof to $\beta_c$ or domain 4 will be considered candidate inhibitory compounds. Thus, the availability of BION-1 as an agent that for the first time allows the direct binding to the cytokine binding region of $\beta_c$ affords a novel test for the identification of simultaneous inhibitors of GM-CSF, IL-3 and IL-5. It will be understood that the same will apply for other cytokines and their respective receptors.

It will be understood that not the entire $\beta_c$ subunit needs be used to screen candidate compounds, and certainly the present data indicates that a fragment of the $\beta_c$ subunit encompassing domain 4 has sufficient structure in common with the native $\beta_c$ subunit to reflect the configuration of the cellular target for an inhibitor useful for an in vivo effect.

In a broad form of a fifth aspect, the invention could be said to reside in a cytokine inhibitor capable of simultaneously blocking the binding of $\beta_c$ by IL-3, GM-CSF, and IL-5 made according to the fourth aspect of the invention.

It is thought that compounds that inhibit binding of the IL-3, IL-5 and GM-CSF to the $\beta_c$ will be therapeutically useful for intervention in conditions where IL-3, GM-CSF and IL-5 play a pathogenic role, mainly allergy, asthma, acute and chronic myeloid leukaemias, lymphoma and inflammation including rheumatoid arthritis, breast cancer and prostate cancer.

Similarly for other common cytokine receptors it is thought that antagonists or agonists will be therapeutically useful. gp130 is functionally analogous to $\beta_c$ in that it is a common binding sub-unit and signal transducer for the IL-6, oncostatin M (OSM), ciliary neutrotrophic factor (CNTF), leukaemia inhibitory factor (LIF) and IL-11. It is suggested that raising an antibody against a domain analogous to domain 4 of $\beta_c$ will also lead to blocking of two or more of these cytokines. Antagonism of this receptor system will be useful in inflammation, leukaemia and lymphoma. Antagonists to IL2Rβ/IL2Rα may be useful as immunosuppresants. Antagonists of LIFR may be useful for the prevention of implantation of embryos in uteri. Antagonists of IL4/L-13 will inhibit IgE production and may be useful in treating asthma and allergies.

DETAILED DESCRIPTION OF THE INVENTION

Materials and Methods

Figure 1:
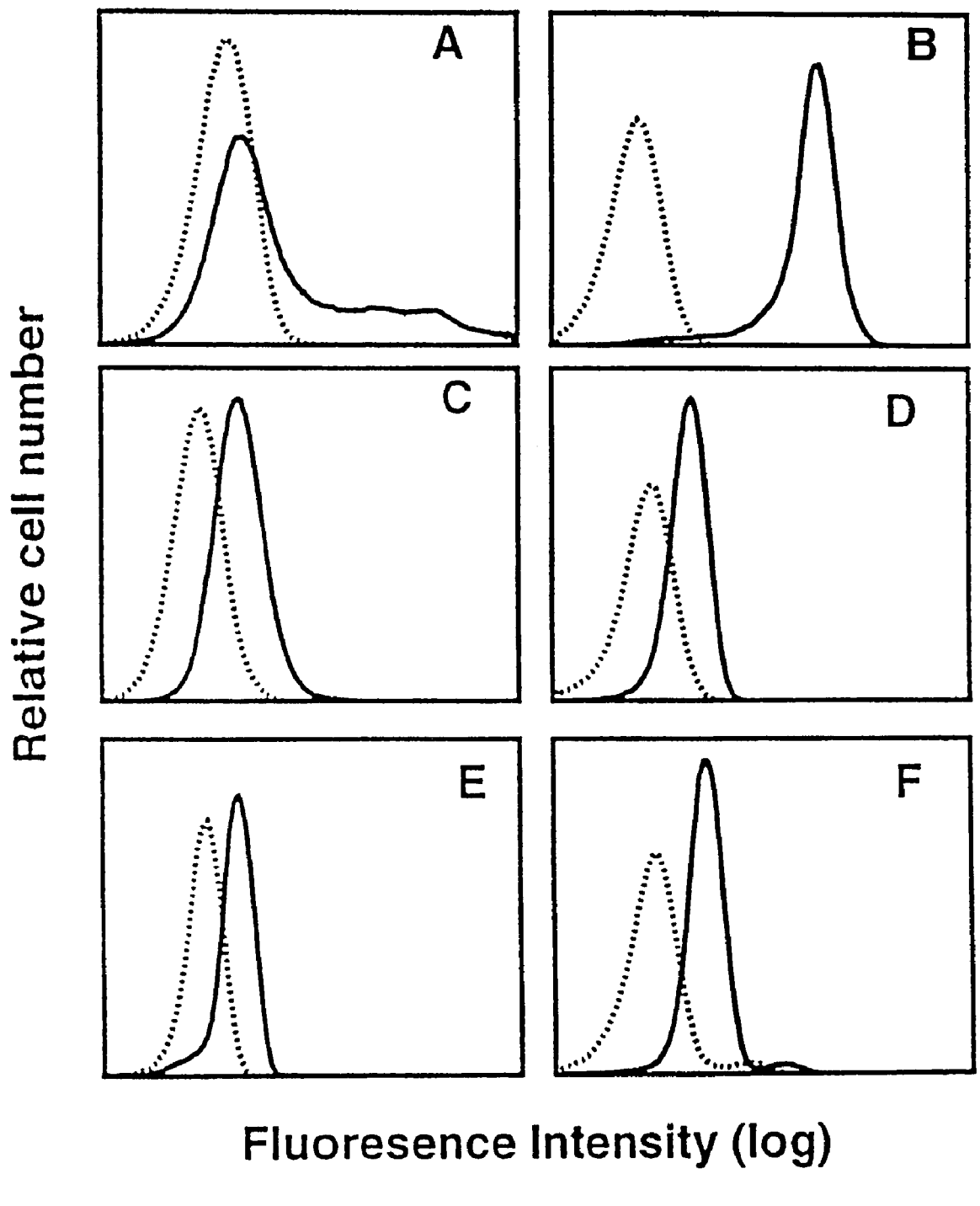
FIG. 1. Flow cytometry analysis of the staining of MoAb BION-1 (continuous line) and an isotype matched IgG$_1$ control MoAb (dotted line) to (A) COS cells transiently transfected with $\beta_c$, (B) CHO cells constitutively expressing $\beta_c$, (C) TF-1.8 cells, (D) neutrophils, (E) eosinophils and (F) monocytes.

ΔQP cDNA: To express domain 4 of $\beta_c$ on the cell surface we cloned the activated $\beta_c$ mutant, h$\beta_c$ΔQP, with an extracellular deletion removing domains 1 to 3 (D'Andrea et al 1996), into the eukaryotic expression vector pcDNA3 (Invitrogen).

Cytokines and cell lines: Recombinant human IL-3 and GM-CSF were produced in *E. coli* as described (Barry et al 1994, Hercus et al 1994b). Recombinant human IL-5 was purified from *E. coli* by Bresatec (Adelaide, South Australia). Recombinant EPO was purchased from Johnson & Johnson (New Jersey). TNFα was a gift from Dr. J. Gamble in the Hanson Centre for Cancer Research. COS cells were transfected with receptor cDNA as described previously (Woodcock et al 1994). CHOβ$_c$ and CHOΔQP cells stably expressing either full length β$_c$ or domain 4 respectively were generated by electroporation (Hercus et al, 1994a). TF1.8 cells were a gift from Dr J. Tavernier from University of Gent, Belgium. MO7e cells, a human megakaryoblastic cell line, were from Dr P Crozier, Aukland, New Zealand. Human eosinophils were purified from the peripheral blood of slightly eosinophilic volunteers via sedimentation through dextran and centrifugation through a discontinuous density gradient of hypertonic Metrizamide, as previously described (Vadas et al 1979). Eosinophils were more than 92% pure. Human neutrophils and monocytes were purified from peripheral blood as described previously (Lopez et al, 1990) with more than 95% purity.

Generation of anti-β$_c$ MoAbs: BALB/c mice were immunized intraperitonally with 1×10$^7$ COS cells transfected with β$_c$ or ΔQP expression constructs. ΔQP constructs express substantially only domain 4 of the extracellular domains of β$_c$. The immunizations were repeated 4 times at two-weekly intervals. Four weeks after the final immunization, a mouse was boosted with 2×10$^6$ COS transfectants intravenously. Three days later, splenocytes were harvested and fused with NS-1 myeloma cells as previously described (Sun et al 1996). Hybridoma supernatants were screened on CHO β$_c$ or CHO ΔQP cells by flow cytometry, with untransfected CHO cells as a control. All antibodies were from single hybridoma clones as selected by limiting dilution method. MoAbs were purified from ascites fluid or hybridoma supernatant by a protein A sepharose column. The isotypes of MoAbs were tested with a Mouse MoAb Isotyping Kit (Boehringer Mannheim, Germany). Fab fragments were generated using a Fab Preparation kit (Pierce, Rockford, Ill.) following the supplied protocol.

Immunofluorescence: Freshly purified neutrophils, eosinophils, monocytes, or CHO and COS cell transfectants (5×10$^5$) were incubated with 50 µl of hybridoma supernatant or 0.25 mg of purified MoAb for 45-60 min at 4° C. Cells were washed twice and then incubated with FITC-conjugated rabbit anti-mouse Ig (Silenus, Hawthorn, Victoria, Australia) for another 30-45 min. Cells were then washed and fixed before analysing their fluorescence intensity on an EPICS-Profile II Flow Cytometer (Courter Electronics). Two colour staining was carried out by additional incubation with another MoAb directly coupled to PK.

Ligand Binding Assay: IL-3 and GM-CSF were radio-iodinated by the iodine monochloride method (Contreras 1983). $^{125}$I-IL-5 was purchased from Dupont NEN (North Sydney, NSW, Australia). Binding assays were performed as previously described (Lopez et al 1989). Briefly, 1-2×10$^6$ TF-1.8 cells were preincubated with BION-1 Fab fragments, anti-β$_c$ or control MoAbs over a concentration range of 0.06 to 4200 nM for 1 hour. Radio-labelled ligand was then added and incubated for a further two hours before the cells were separated from free label by spinning through FCS. Counts associated with the resulting cell pellets were determined by counting on a γ counter (Cobra Auto Gamma; Packard Instruments Co, Meridien, Conn.). Non-specific binding was determined for each ligand by binding in the presence of a 200 fold excess of unlabelled cytokine.

MoAb binding assay: MoAbs were radio-iodinated by the chloramine-T method (McConahey 1980). Saturation binding studies were performed by incubating 2×10$^6$ TF1 cells in a range of concentrations of radio-labelled antibodies in the presence or absence of excess unlabelled antibodies. The binding affinity of each anti-β$_c$ MoAb to its antigen was determined by Scatchard transformation (Scatchard 1949) and analysed with the ligand program (Munson and Rodbard, 1980). Competition binding experiments were set up by pre-incubating the TF1.8 cells with a range concentration of IL-3, or GM-CSF, or IL-5 prior to adding radio-labelled MoAb QP1 for two hours as per ligand binding assay. Epitope analysis was determined by testing the capacity of each unlabelled MoAb to compete for the binding of each radio-labelled MoAb to the β$_c$ on COS cell transfectant.

Co-immunoprecipitation of α and β chains and the β$_c$ phosphorylation assays: M07e cells were surface labelled with $^{125}$I by the lactoperoxidase method as described previously (Walsh and Crumpton, 1977). The labelled cells incubated in either medium containing IL-3 (100 ng/ml) alone or IL-3 together with the MoAb QP1, 1C1 (0.5 mg/ml) or 7G3 (30 mg/ml) for 5 min. Cells were lysed in lysis buffer consisting of 137 mM NaCl, 10 mM Tris-HCl (pH 7.4), 10% Glycerol, 1% Nonindet P40 with protease and phosphatase inhibitors (10 mg/ml leupeptin, 2 mM phenylmethylsulphonyl fluoride, 10 mg/ml aprotonin and 2 mM sodium vanadate) for 30 min at 4° C. followed by centrifugation of the lysate at 10,000×g for 15 min to remove cellular debris. The lysate was precleared with mouse-Ig-coupled Sepharose beads for 18 h at 4° C. and incubated with anti-IL-3Ra, anti-β$_c$ MoAb beads for 2 hr at 4° C. The beads were washed 6 times with lysis buffer and immunoprecipitated proteins were separated by SDS-PAGE under reducing condition. The immunoprecipitated proteins were detected by a PhosphorImager (Molecular Dynamics, Sunnyvale, Calif.). The gels were then reprobed by Western blotting analysis with an anti-phosphotyrosine MoAb, 3-365-10 (Boehringer Mannheim, Frankfurt, Germany).

TF-1.8 cell proliferation assay: TF-1.8 cells were grown in the presence of 2 ng/ml of GM-CSF. The cells were starved for 24 hours before setting up proliferation assays as described previously (Sun et al., 1996). From dose-response curves the half-maximal proliferation dosage of IL-3 (0.3 ng/ml), GM-CSF (0.03 ng/ml), IL-5 (0.3 ng/ml) or EPO (5 ng/ml) was chosen to perform proliferation experiments in the presence of a range of concentrations of MoAbs. The $^3$H-Thymnidine incorporation of each sample was determined by liquid scintillation and expressed as disintegrations per minute (DPM).

Eosinophil survival assays: The maximal dose of IL-5 required to support eosinophil survival after 36 hours was determined. Eosinophils were then cultured with 1 nM of IL 5 plus anti-β$_c$ MoAbs for 36 hours. The viability of eosinophils was quantitated by propidium iodide staining and flow cytometry analysis as described (Nicoletti, 1991).

CD69 expression: CD69 expression on eosinophils was measured by means of an antiCD69 monoclonal MoAb coupled to PE by flow cytometry.

β$_c$ mutants and MoAb Mapping: Single amino acid substitutions in the B'-C' and F'-G' loops of domain 4 of the β$_c$ have been described previously (Woodcock, et al., 1994; 1996). The cDNAs for wild type β$_c$ and each of the β$_c$ mutants in the B'-C' and F'-G' loops were introduced into COS cells by the electroporation (Hercus et al., 1994). Cell transfectants were analysed for surface expression with 48 hours after transfection. Mutants on the B' and C' β-strands such as L356N, W358N, I374N and Y376N were expressed on FDCP1 cells from retroviral expression constructs (Jenkins et al., 1995). Epitope-mapping of anti-sc antibodies was analysed by Immunofluorescent study. The anti-$\beta_c$ MoAbs were tested for their abilities to recognise wild type $\beta_c$ and the $\beta_c$ mutants analysed by flow cytometer using standard immunofluorescence method. For each mutant, the experiment was repeated at least twice.

BION-1 binding inhibitory peptides: *E. coli* derived soluble $\beta_c$ domain 4 (s$\beta_c$#4) was coupled to Maxisorp ELISA plates at 10 µg/1 ml in 0.1M carbonate buffer overnight and then blocked with 1% BSA. B45.pep (FHWWWQP-GGGCDYDDDK) was derived from four rounds of biopanning the Ph.D-7mer library with s$\beta_c$#4 using an acid eluant. YB12.pep (FPFWYHAHSPWS-GGGCDYKDDDK) was derived from biopanning the Ph.D-12mer library with s$\beta_c$#4 using an acid eluant. B45 was allowed the bond to s$\beta_c$#4 at 0.0125 µM and YB12 was allowed to bind s$\beta_c$#4 at 0.025 µM. The plate was washed in TBS+0.5% Tween. BION-1 was added to the plates at a starting concentration of 5 µg/ml and serial dilutions were used to titrate the BION-1 down to 0.004 µg/ml.

The plate was washed again and BION-1 binding to s$\beta_c$#4 was detected with α-mouse conjugated to HRP, using a colour based reaction which was read on a plate counter by absorption.

BION-1 inhibition of chronic myelomonocytic cells: Peripheral blood from a patient with chronic myelomonocytic leukemia was centrifuged over Ficoll-Paque to separate the mononuclear cells. After washing and counting, the cells were plated on agar as a concentration of $10^5$ per plate. After incubation in medium containing monoclonal antibodies BION-1 or 1C1, with or without IL-3, for 14 days at 37° C. the number of arising colonies were counted by mycroscopical examination. Each cell cluster containing more than 40 cells was counted as a colony.

Results

Development of MoAb BION-1

Previous experiments have shown that the putative F'-G' loop of $\beta_c$ contains a common binding site for IL-5, GM-CSF and IL-3 (Woodcock et al, 1996; WO 97/28190). We have now produced a blocking compound, represented by MoAb BION-1, by immunizing mice with COS cells transfected with a cDNA coding for domain 4 of $\beta_c$. Screening of hybridoma supernatants was performed on a CHO cell line expressing domain 4 of $\beta_c$. One hybridoma cell line was identified which produced a MoAb which specifically recognized this cell line and not a parental CHO cell line not expressing domain 4 of $\beta_c$. This MoAb was termed BION-1 and was characterized in biochemical, binding and biological experiments.

BION-1 Recognizes Domain 4 as Well as Wild Type $\beta_c$.

MoAb BION-1 was tested for reactivity against cell lines transfected with $\beta_c$ and against primary cells known to express IL-5, GM-CSF and IL-3 receptors. BION-1 recognized COS cells transiently transfected with $\beta_c$ CHO cells permanently transfected with $\beta_c$, the erythroleukaemic TF-1 cell line, and purified peripheral blood human neutrophils, eosinophils and monocytes (FIG. 1).

Figure 2:
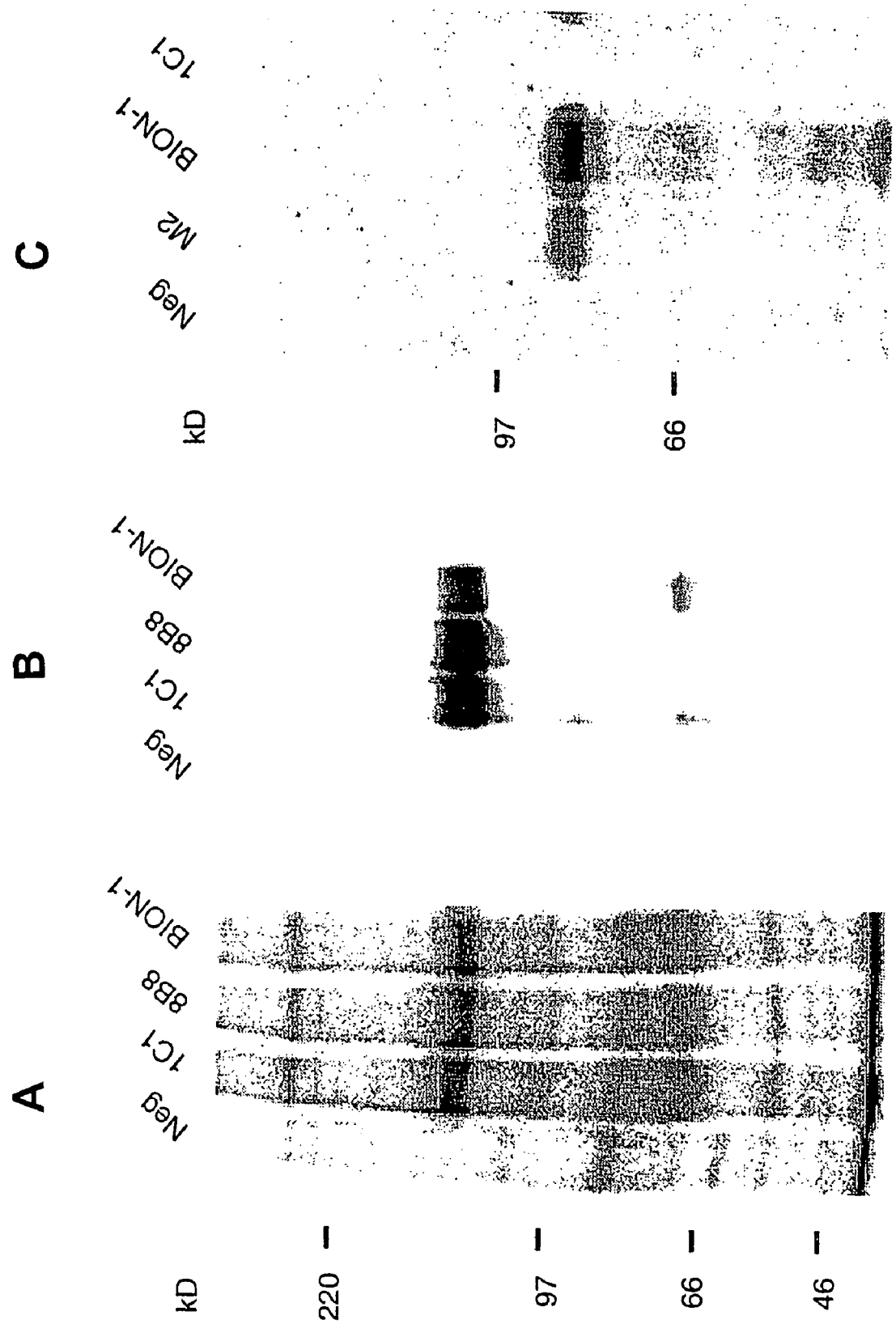
FIG. 2. MoAb BION-1 recognizes $\beta_c$ protein. (A) Immunoprecipitation of $\beta_c$ from $^{125}$I-surface labelled CHO $\beta_c$ cell lysate. Both experiments were performed on 7.5% SDS PAGE under reducing conditions. (C) MoAb BION-1, but not another anti-$\beta_c$ MoAb 1C1, recognises a $\beta_c$ mutant ($\beta_c$-ΔQP) that contains only domain 4 in the extracellular regions by immunoprecipitation of CHO ΔQP cells. This mutant has a flag attached so it can also be seen by anti-flag MoAb M2. The experiment was performed on 10% SDS PAGE under reducing conditions.

The antigen recognized by BION-1 was confirmed to be domain 4 of $\beta_c$, by biochemical analysis of transfected cells. FIG. 2A shows that BION-1 immunoprecipitated a surface $^{125}$I-labelled protein of about 120,000 MW consistent with the size of $\beta_c$. Similarly, BION-1 recognized a protein of 120,000 MW by Western blotting using lysates of CHO cells expressing full length wild type $\beta_c$ (FIG. 2B). The size of these bands also corresponded to the bands recognized by a previously developed anti-$\beta_c$ MoAb (Korpelainen et al 1993; Woodcock et al, 1996). To formally show that BION-1 recognized domain 4 of $\beta_c$ we also tested BION-1 for its ability to immiinoprecipitate domain 4 expressed on the surface of CHO cells. As a positive control we incorporated a short polypeptide to the N-terminus of domain 4 (flag epitope) to which a MoAb has been previously developed. As a negative control, we used the anti-$\beta_c$ MoAb 1C1 which recognizes an epitope located elsewhere in $\beta_c$. FIG. 2C shows that BION-1 immunoprecipitated a band of about 80,000 MW from $^{125}$I-surface labelled-domain 4-expressing CHO cells consistent with the expected size of domain 4. MoAb M2 against the flag epitope added to domain 4 of $\beta_c$ also precipitated a similar size protein. In contrast, MoAb 1C1 failed to immunoprecipitate domain 4. These experiments show that BION-1 can specifically recognize domain 4 of $\beta_c$ on the surface of cells and following denaturation of the protein.

Figure 3:
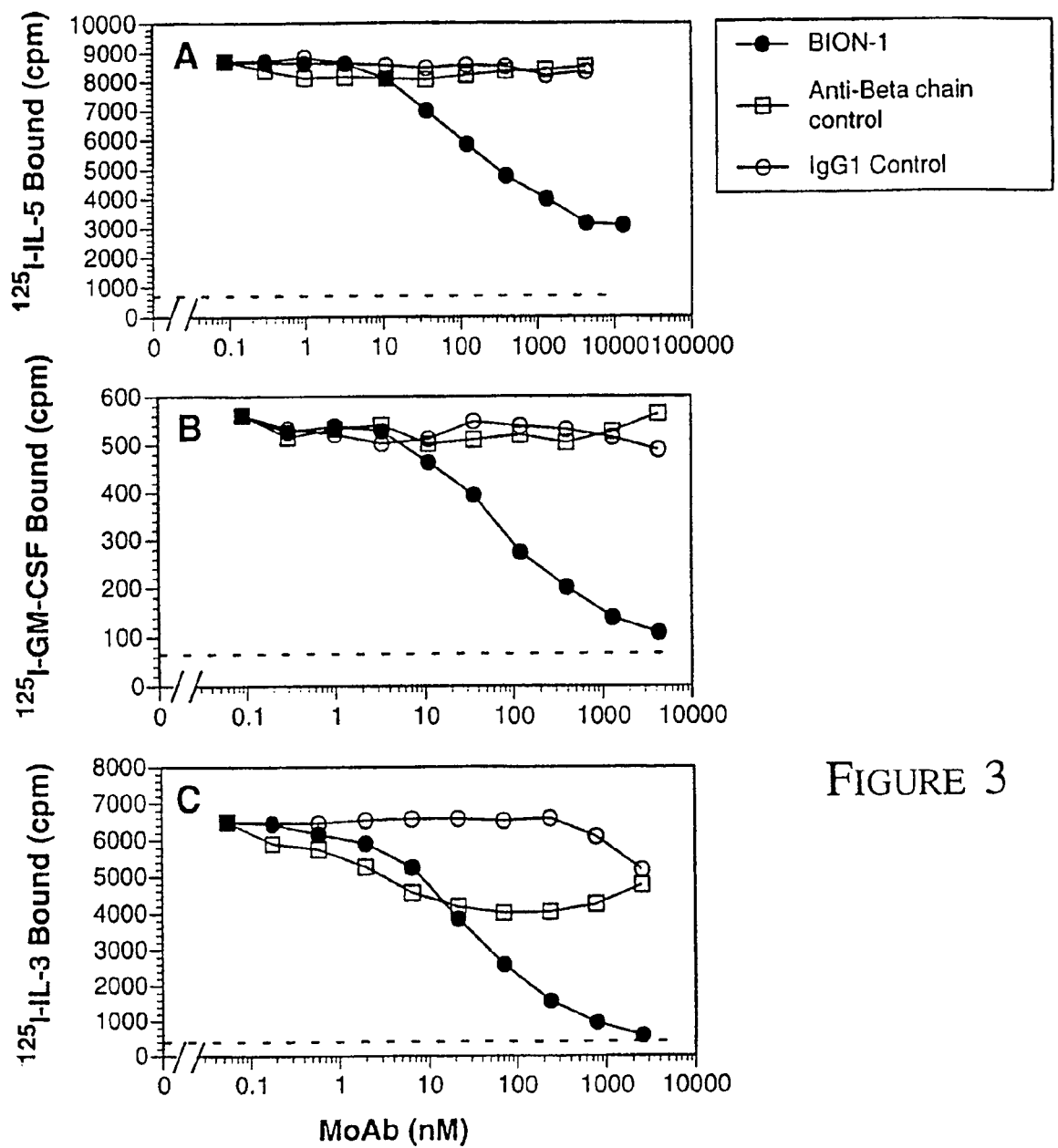
FIG. 3. Dose-dependent competition for the binding of $^{125}$I-IL-5 (50 pM), $^{125}$I-GM-CSF (50 pM) and $^{125}$I-IL-3 (200 pM) by MoAbs BION-1 (•), an anti-$\beta_c$ MoAb control ( ), and an IgG$_1$ control MoAb (o) to TF-1.8 cells (2×10$^6$ per point). ( - - - ) represents ligand binding in the presence of 200-fold excess unlabelled ligand. Each point is the mean of triplicate determinations.

BION-1 Inhibits the High Affinity Binding of IL-5. GM-CSF and IL-3 to TF-1 Cells and to Human Eosinophils Given that domain 4 of $\beta_c$ is crucial for the high affinity binding of IL-5, GM-CSF and IL-3, we examined whether BION-1 was able to affect this binding. We found that BION-1 inhibited in a dose-dependent manner the binding of $^{125}$I-IL-5, $^{125}$I-GM-CSF and $^{125}$I-IL-3 to the human erythroleukaemic cell line TF-1. For each radioligand we used the smallest possible concentration to maximize the possibility of measuring high affinity. This can be more readily achieved with IL-3 and GM-CSF for which the difference between the low affinity component (provided by each α chain alone) and the high affinity component (provided by co-expressing $\beta_c$ with each α chain) is about 1,000 fold and 30 fold respectively. In the case of IL-5, the affinity conversion of $\beta_c$ is only in the 25 fold range, hence, high and low affinity binding cannot be clearly separated. This is likely to explain why BION-1 shows complete inhibition of $^{125}$I-GM-CSF and $^{125}$I-IL-3 binding (FIG. 3). The residual $^{125}$I-IL-5 binding seen with high concentrations of BION-1 is likely to be the result of low affinity $^{125}$I-IL-5, binding (α chain) which BION-1 would not be expected to inhibit. This is consistent with BION-1 inhibition of $^{125}$I-IL-5, binding reaching a plateau beyond which no further inhibition can be detected (FIG. 3a). Other anti-$\beta_c$ MoAb (anti-,$\beta_c$ control) and the IgG$_1$ MoAb control did not inhibit $^{125}$I-IL-5, $^{125}$I-GM-CSF and $^{125}$I-IL-3 binding to TF-1 cells (FIG. 3).

Figure 4:
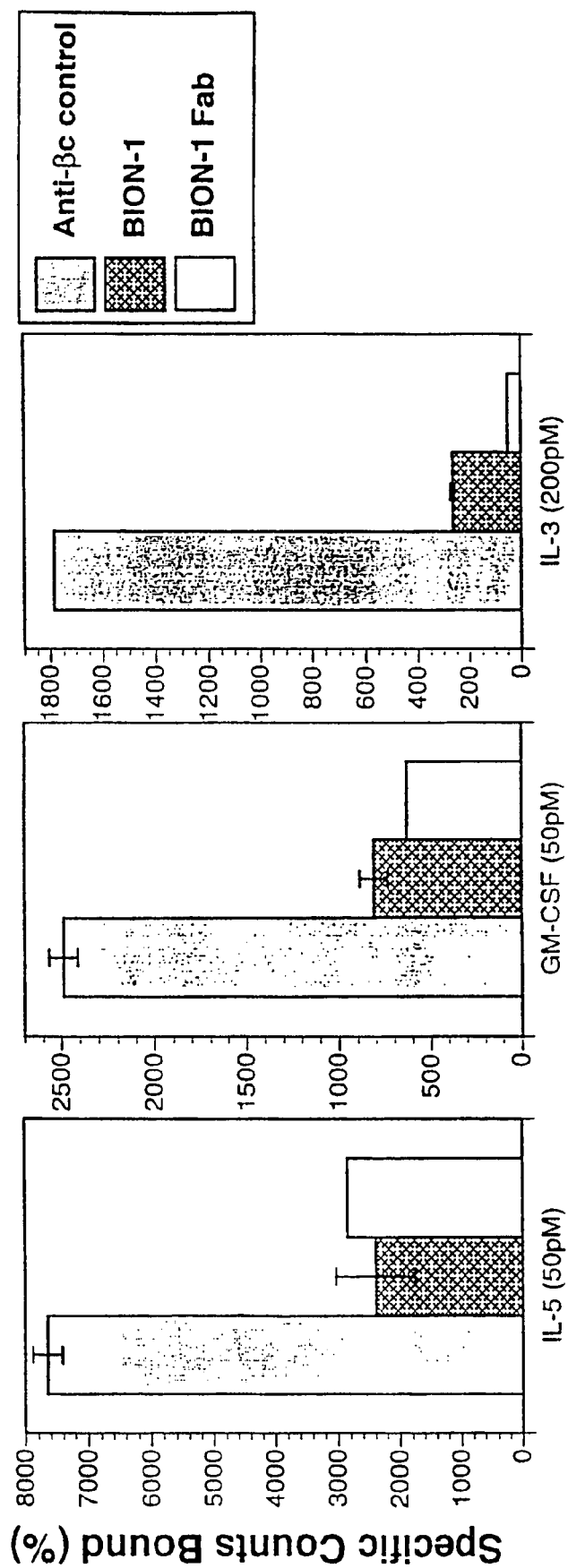
FIG. 4. A Fab fragment of BION-1 blocks high affinity binding of IL-5, GM-CSF and IL-3. Binding of $^{125}$I-IL-5 (50 pM), $^{125}$I-GM-CSF (50 pM) and $^{125}$I-IL-3 (200 pM) were assessed on TFI.8 cells (2×10$^6$ per point) in the presence or absence of 3000 nM MoAb BION-1, or control anti-$\beta_c$ MoAb, or 4200 nM Fab fragment of BION-1 for 2 h at room temperature. 1C1 was used as a non blocking anti-$\beta_c$ control. Cells were separated from unbound radioligand by spinning through FCS and the resulting cell pellet was counted. The results are expressed as a percentage of the total specific cpm bound seen in the absence of antibody. Non-specific binding was determined in the presence of 200 fold excess of cold ligand. Total binding seen for $^{125}$I-IL-5, $^{125}$I-GM-CSF and $^{125}$I-IL-3 were 9744.2, 2567.1 and 3379.13 cpm respectively. Blocking with Fab fragment of BION-1 was determined from a single point and BION-1 and 1C1 values are the mean of duplicate determinations with error bars representing 1 standard deviation.

The blocking effect of BION-1 was seen whether the MoAb was used as purified IgG or as Fab' fragment. FIG. 4 shows that the Fab' fragment of BION-1 blocked the binding of 50 pM $^{125}$I-IL-5, 50 pM $^{125}$I-GM-CSF and 200 pM $^{125}$I-IL-3 to TF-1 cells.

Figure 5:
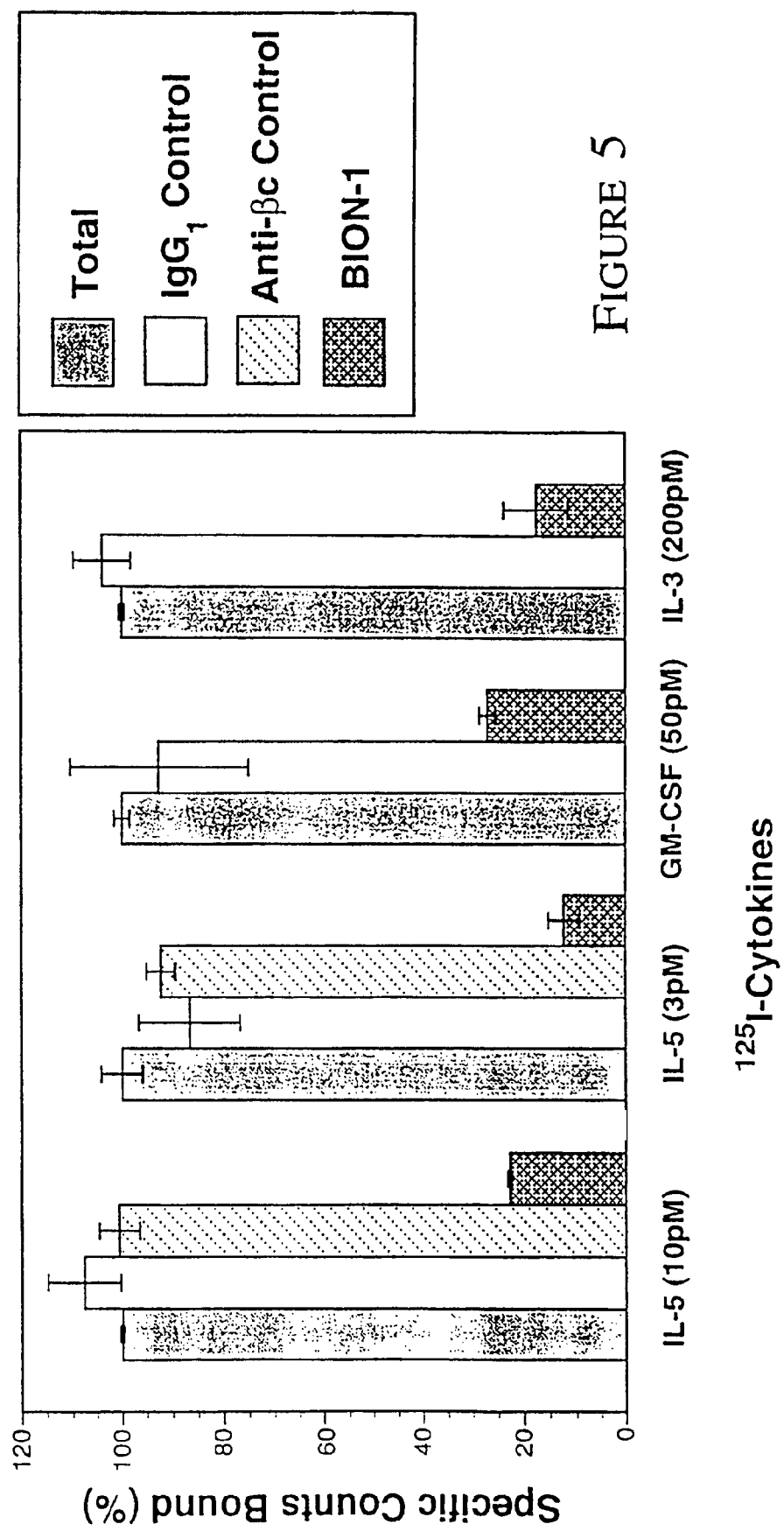
FIG. 5. BION-1 blocks high affinity binding of IL-5, GM-CSF and IL-3 to human eosinophils. Human eosinophils (1.8×10$^6$ per point) were incubated with $^{125}$I-IL-5 (10 pM or 3 pM), $^{125}$I-GM-CSF (50 pM) or $^{125}$I-IL-3 (200 pM) either alone or in the presence of 1 µM MoAb at room temperature for 2 h. MoAb's 9E10 and 8E4 were used as isotype matched and non-blocking anti-$\beta_c$ control respectively for BION-1. Cells were separated from unbound radioligand by spinning through FCS and the resulting cell pellet was counted. The results are expressed as a percentage of the total specific cpm bound seen in the absence of antibody. Non-specific binding was determined in the presence of 200 fold excess of cold ligand and was determined to be an average of 0.3% of total counts added. Total binding seen for $^{125}$I-IL-5, $^{125}$I-GM-CSF and $^{125}$I-IL-3 were 765, 622 and 748 cpm respectively. Each point is the mean of duplicate determinations and error bars represent 1 standard deviation.

Since one of the major clinical utilities of blocking IL-5, GM-CSF and IL-3 binding is likely to be in asthma, a disease in which eosinophils are believed to play a major role, it was important to test whether BION-1 could block the binding of IL-5, GM-CSF and IL-3 to these cells. As shown in FIG. 5, BION-1 inhibited the binding of all three radio-labelled cytokines to purified human eosinophils. In contrast, other anti-$\beta_c$ MoAb or the IgG$_1$ MoAb control failed to do so.

Epitope Mapping of BION-1

Figure 6:
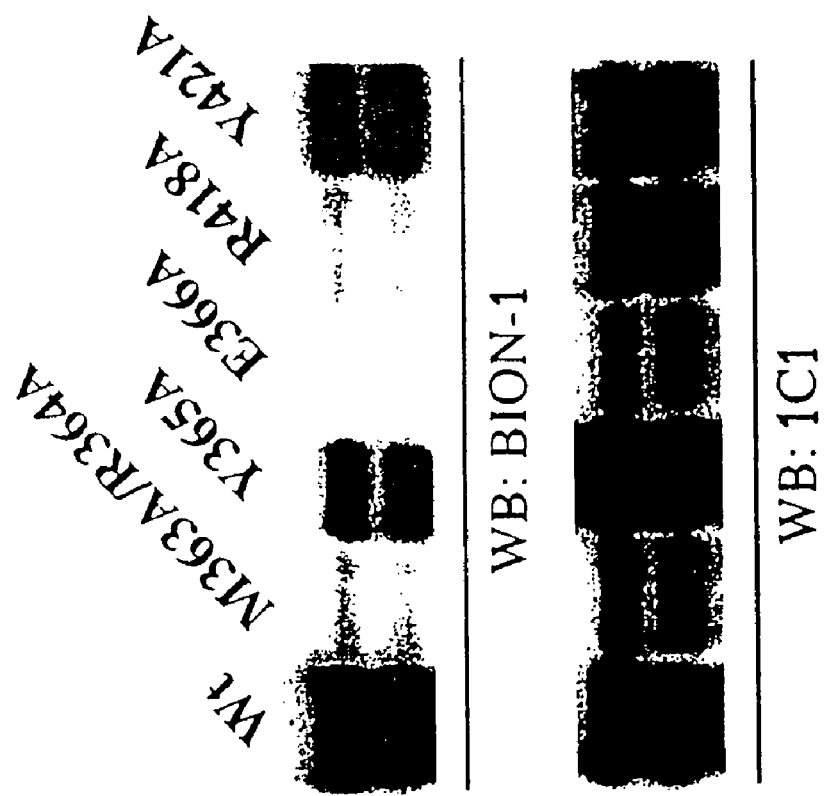
FIG. 6. MoAb BION-1 recognizes an epitope in $\beta_c$ comprising at least residues M363, R364, E366 and R418. Human $\beta_c$ wild type and mutants (Woodcock et al, 1996) were tested for reactivity with MoAb BION-1 and 1C1 used as a control. Following expression of wild type $\beta_c$ and $\beta_c$ mutants on COS cells, $\beta_c$ was immunoprecipitated by MoAb 8E4, followed by Western blotting by MoAb BION-1 (top) or the non blocking MoAb 1C1 (bottom).

The fact that BION-1 inhibited the binding of $^{125}$I-IL-5, $^{125}$I-GM-CSF and $^{125}$I-IL-3 to TF-1 cells and eosinophils suggested that it might be binding to the critical region in $\beta_c$ to which these cytokines bind or at least in close proximity to it. To try to define the region/epitope in $\beta_c$ recognized by BION-1, we used several mutants of $\beta_c$ and examined whether substitutions of individual amino acids in the predicted B'-C' loop or F'-G' loop impaired BION-1 binding. Two sets of experiments were carried out. In the first instance we immunoprecipitated wild type $\beta_c$ from transfected COS cells with a MoAb anti-$\beta_c$. The immunoprecipitates were then tested for reactivity with the control anti-$\beta_c$ MoAb 1C1, or BION-1. The results shows that $\beta_c$ mutants carrying the substitutions M363A/R364A, or E366A or R418A were not recognized by BION-1 (FIG. 6). In a second set of experiments, the direct binding of radio-labelled BION-1 was measured on transfectants expressing the same mutants. Similar results were obtained in that whilst 1C1 bound with similar affinity to wild type $\beta_c$ and the $\beta_c$ mutants, BION-1 binding was eliminated by the M363A/R364A, E366A and R418A mutants (Table I). These results suggest that the epitope recognized by BION-1 is formed, at least in part, by M363 and/or R364, E366 and R418. This is consistent with the disclosure in WO 97/28190 that agents that bind the putative F'-G' loop (of which R418 is part of) will be antagonists of IL-5, GM-CSF and IL-3.

BION-1 and IL-3 Reciprocally Inhibit Each Other's Binding

Figure 7:
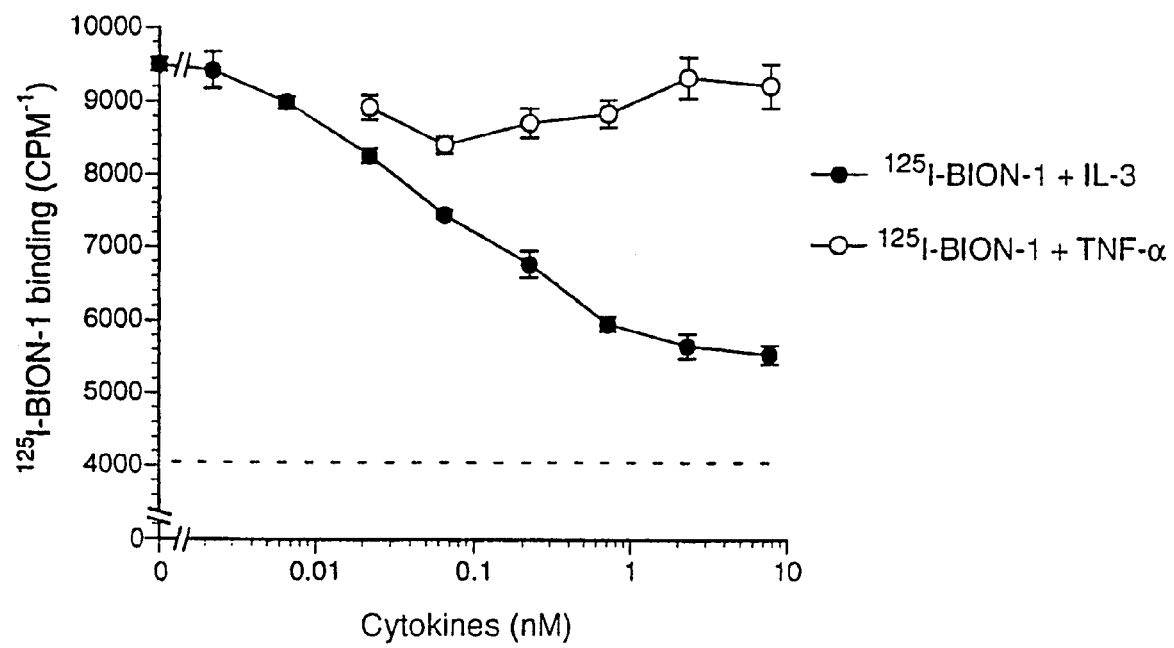
FIG. 7. The binding of $^{125}$I-labelled MoAb BION-1 (1 nM) to TF. 1 cells is inhibited by IL-3 (•), but not by TNF-α(o). ( - - - ) Represents inhibition in the presence of 200-fold excess of unlabelled BION-1.

To confirm that the epitope recognized by BION-1 was the same or close to the binding site utilized by IL-5, GM-CSF and IL-3, we performed the reverse experiment, in which BION-1 was radio-labelled and increasing concentrations of IL-3 used to compete for $^{125}$I-BION-1 binding. The results showed (FIG. 7) that IL-3 competed for $^{125}$I-BION-1 binding in a dose-dependent manner emphasizing the close and intimate proximity of BION-1 and IL-3 binding epitopes in $\beta_c$ BION-1 Specifically Inhibits the Function of IL-5. GM-CSF and DL-3 Including Their Stimulation of Eosinophil Production and Activation.

Figure 8:
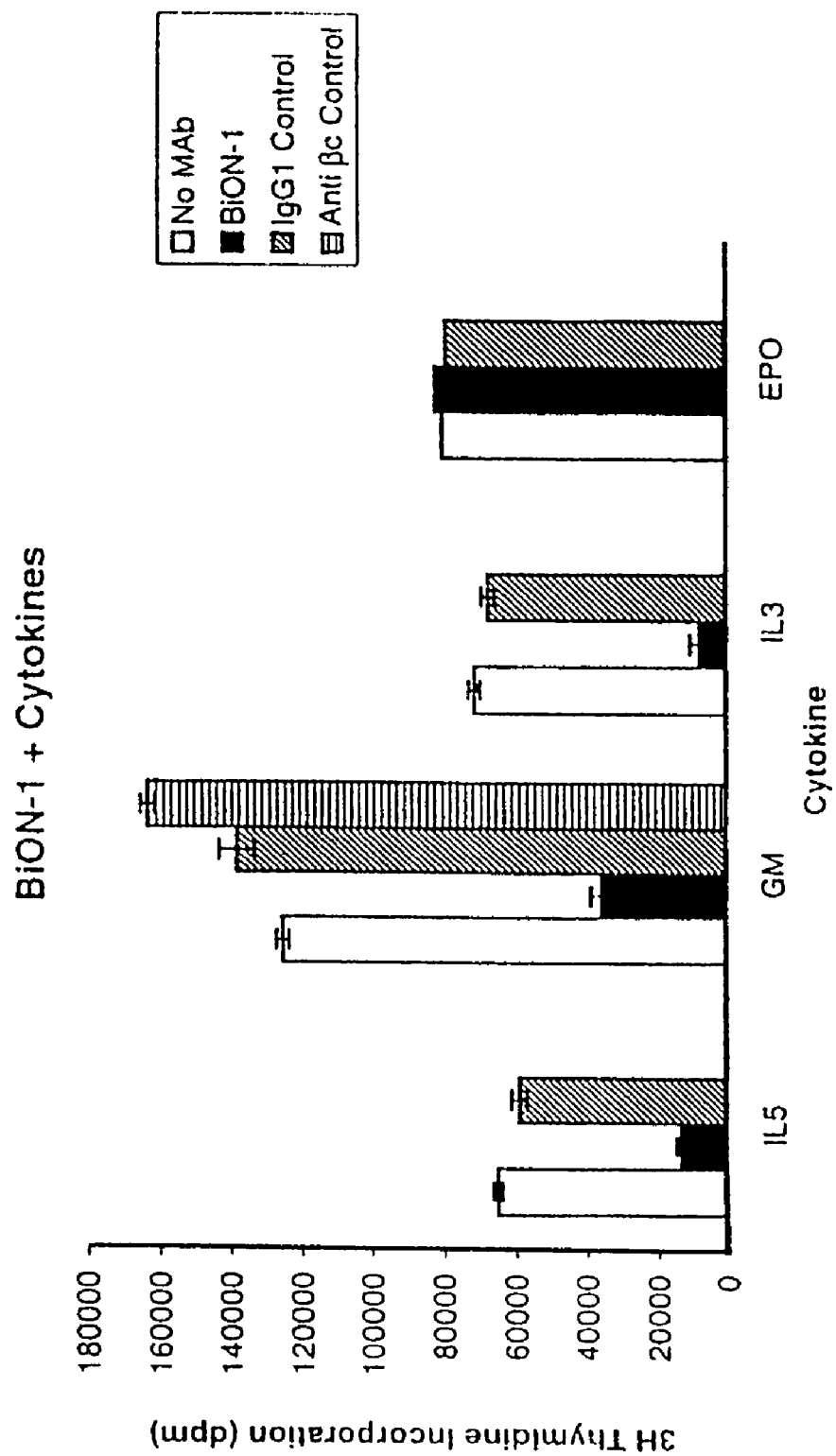
FIG. 8. BION-1 IgG selectively inhibits IL-5, GM-CSF and IL-3 mediated proliferation of TF 1.8 cells. The proliferation experiments represent the comparison of inhibition of BION-1 IgG at maximal dosage (400 µg/ml BION-1 with IL-5 and IL-3 and 850 µg/ml with GM-CSF) against ED$^{50}$ concentrations for IL-5 (0.3 ng/ml), GM-CSF (0.03 ng/ml) or IL-3 (0.3 ng/ml). An anti-$\beta_c$ antibody and an irrelevant IgG antibody were used as controls. The results are expressed as DPM. Each value represents the mean of triplicate determinations and error bars represent the SEM.

To ascertain whether the inhibition of IL-5, GM-CSF and IL-3 binding by BION-1 was translated into inhibition of IL-5, GM-CSF and IL-3 stimulation we used the factor dependent TF-1 cell line. This cell line proliferates in the presence of either IL-5, GM-CSF, IL-3 or erythropoietin (EPO) (FIG. 8). As shown in FIG. 8 MoAb BION-1 but not other MoAb anti-$\beta_c$ nor an IgG, control MoAb inhibited the stimulation of TF-1 cell proliferation by IL-5, GM-CSF and IL-3. In contrast, the stimulating ability of erythropoietin was not inhibited showing specificity of BION-1 for the IL-5/GM-CSF/IL-3 receptors system.

Figure 9:
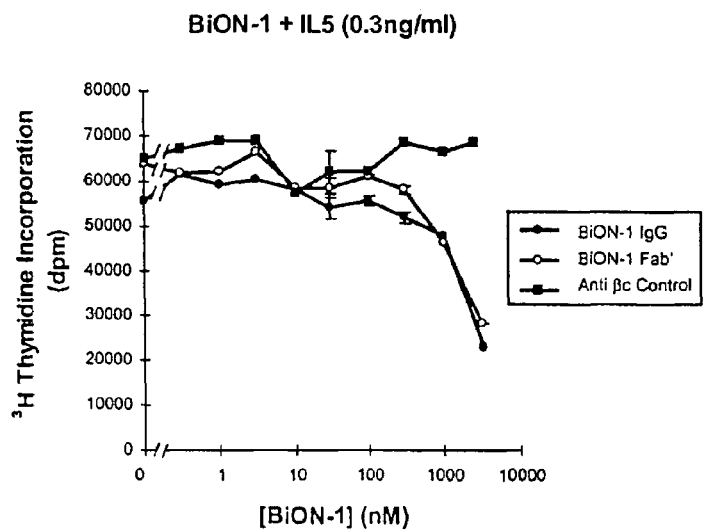
FIG. 9. Fab fragment of BION-1 and BION-1 IgG inhibits IL-5, GM-CSF and IL-3 mediated proliferation of TF1.8 cells. Intact IgG or Fab fragment of BION-1 were titrated against a fixed concentration of IL-5 (0.3 ng/ml), GM-CSF (0.03 ng/ml) or IL-3 (0.3 ng/ml) in proliferation assays where TF1.8 cells at 5×10$^4$/well were incubated for 48 hours and then pulsed for 5 hours with 0.5 µCi/well $^3$H-Thymidine. The results are expressed as DPM. Each value represents the mean of triplicate determinations and error bars represent the SEM.
Figure 9:
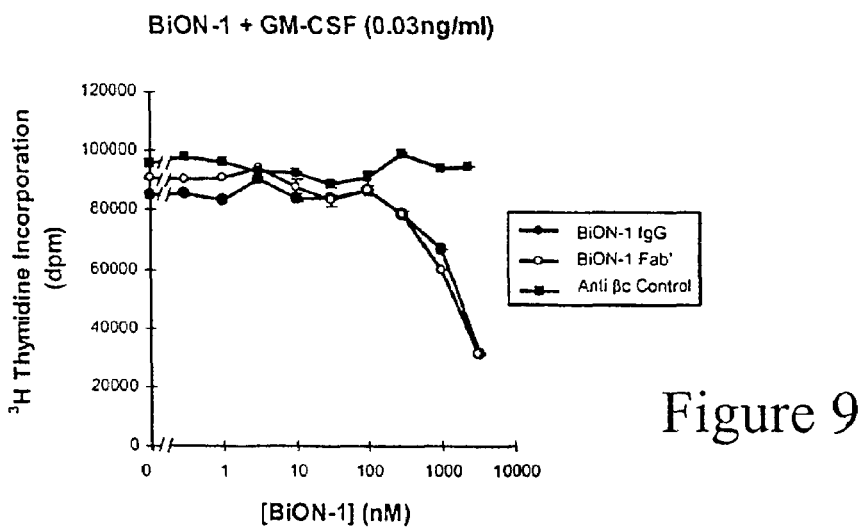
Figure 9:
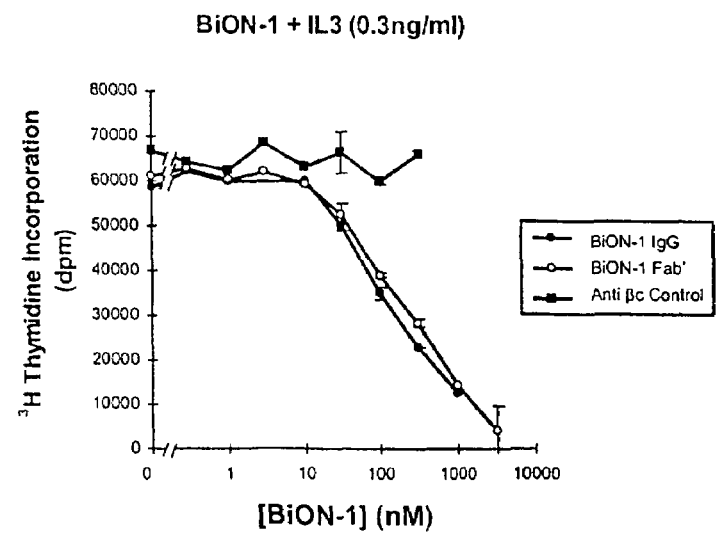

Titration experiments showed that BION-1 inhibited cytokine-mediated TF-1 cell proliferation in a dose-dependent manner with an ED$_{50}$ of about 100-300 nM (FIG. 9). FIG. 9 also shows that other anti-$\beta_c$ MoAb were not inhibitory, and that Fab fragments of BION-1 behaved similarly to BION-1 as a whole IgG with virtually overlapping ED$_{50}$ values.

Since eosinophils are believed to be the major effector cells in asthma and they respond to IL-5, GM-CSF and IL-3, we examined BION-1 for its ability to block eosinophil production, eosinophil survival and eosinophil activation in response to these three cytokines. We found that BION-1 but not MoAb 8E4 inhibited the ability of IL-5, GM-CSF and IL-3 to stimulate the formation of eosinophil colonies from human bone marrow cells (Table II).

Figure 10:
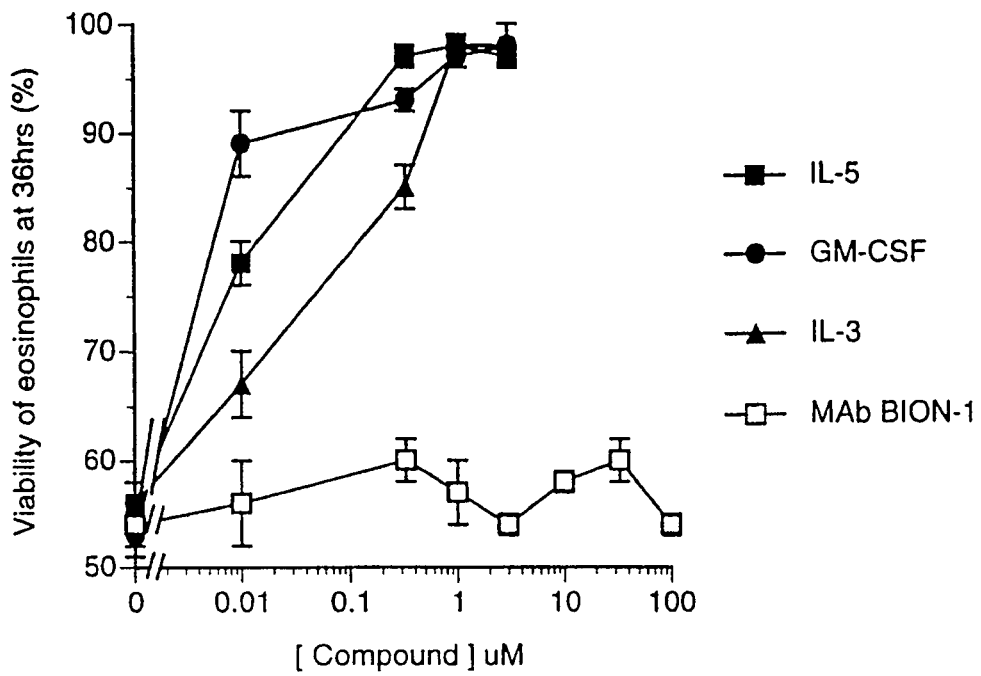
FIG. 10. Eosinophil survival. (A) Viability of eosinophil after 36 hours in the presence of IL-5, IL-3 and GM-CSF. (B) Viability of eosinophil after 36 hours in the presence of IL-5, IL-3 and GM-CSF (1 nM) and different concentrations of MoAb BION-1 (o) and 8E4 (•). Each point is the mean of triplicate determinations from three samples and error bars represent 1 standard deviation.
Figure 10:
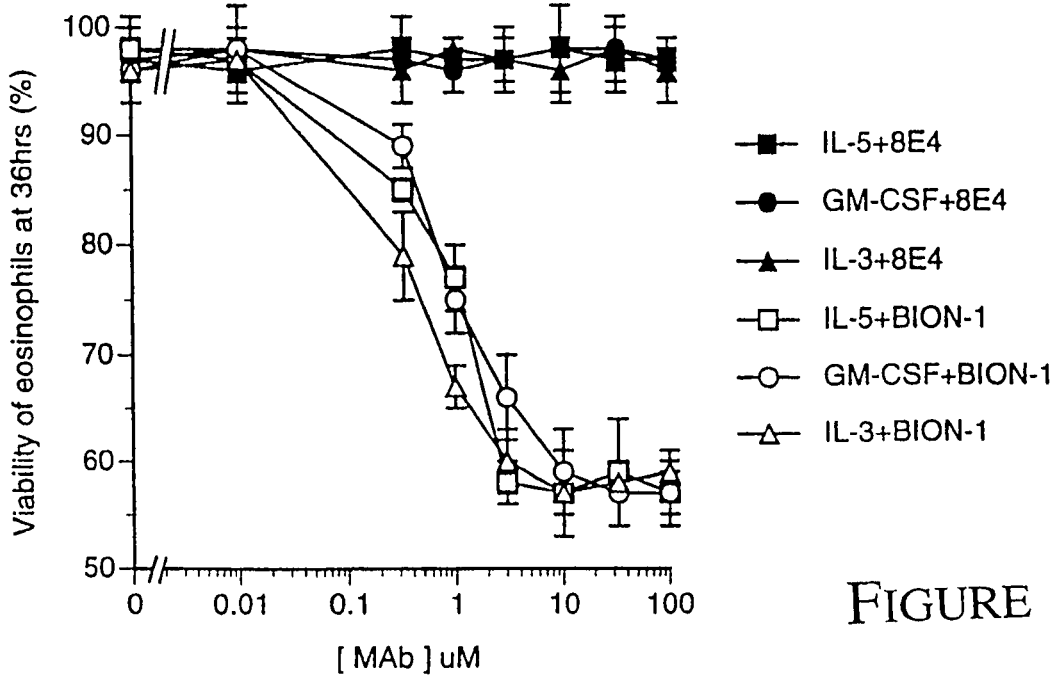
Figure 11:
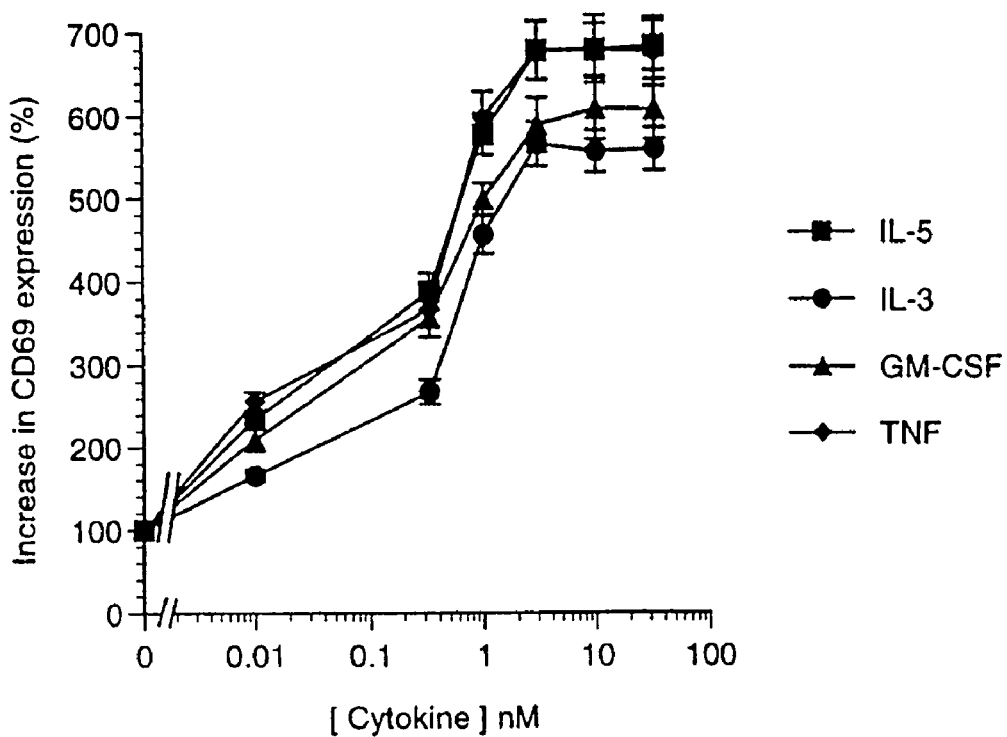
FIG. 11. MoAb BION-1 inhibits IL-5-stimulated CD69 up-regulation on human eosinophils. (A) CD69 up-regulation in the presence of different concentrations of IL-5, IL-3, GM-CSF and TNF-α. (B) CD69 up-regulation stimulated by 1 nM of IL-5, GM-CSF, IL-3 or TNF-α in the presence of different concentrations of MoAb BION-1 or control anti-$\beta_c$ MoAb 8E4. Each point is the mean value of three replicates and error bars represent 1 standard deviation.
Figure 11:
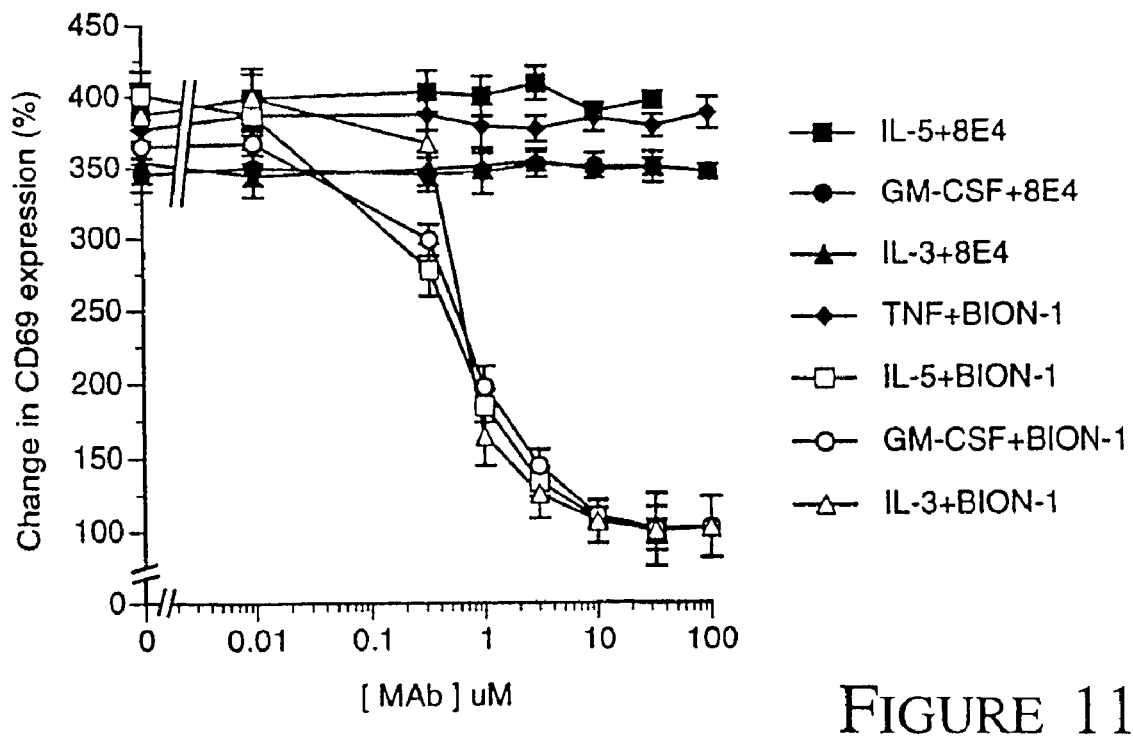

Importantly, BION-1 inhibited the pro survival activity of IL-5, IL-3 and GM-CSF on purified peripheral blood human eosinophils. Whilst these cytokines are essential for maintaining eosinophil viability (FIG. 10A), blocking of $\beta_c$ by MoAb BION-1 promotes eosinophil cell death to levels similar to those observed in the absence of cytokines (FIG. 10B). Eosinophils can be activated by IL-5, GM-CSF and IL-3 as well as by tumour necrosis factor (TNF-$\alpha$), a factor that operates through the TNF-$\alpha$ receptor. A sign of eosinophil activation is the upregulation of the CD69 surface antigen, a phenomenon induced by all four cytokines (FIG. 11A). Using this activation system we found that BION-1 inhibited the activation of eosinophils by IL-5, GM-CSF and IL-3 (FIG. 11B). Other MoAb anti-$\beta_c$ or IgG$_1$controls failed to do so. In addition the blocking effect of BION-1 was found to be specific in that the stimulating activity of TNF-$\alpha$ was not inhibited (FIG. 11B).

BION-1 Specifically Inhibits IL-3 Receptor Dimerization and Activation

Figure 12:
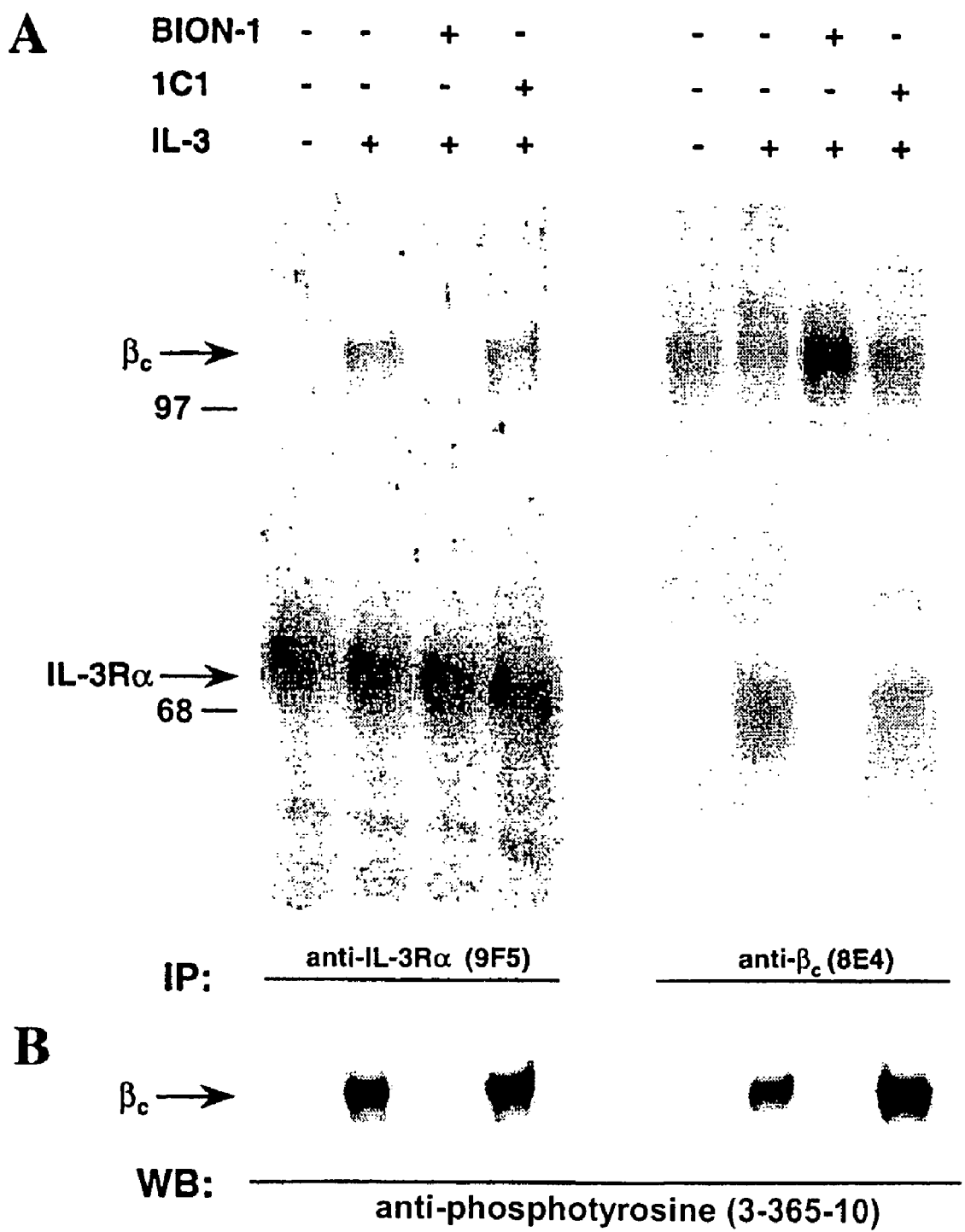
FIG. 12. Inhibition of L-3-induced α and β chain dimerization and phosphorylation by MoAb BION-1. Immunoprecipitations using anti-IL-3Rα MoAb 9F5 or anti-$\beta_c$ MoAb 8E4 from M07e cells preincubated with MoAbs BION-1, MoAb 1C1 or medium alone (−) for 1 min, before being stimulated (+) or not (−) with IL-3 (50 nM) for 5 min. The figure was visualised by PhosphorImaging and the position and molecular weight (in thousands) of marker proteins are shown to the left of the gels. The gels were reprobed by Western blotting analysis using anti-phosphotyrosine MoAb 3-365-10 and the top panel shows the image of part of the gels in the $\beta_c$ area.

In order to define the mechanism of BION-1 antagonism we examined BION-1 for its ability to influence receptor dimerization and activation. We have previously shown that IL-3 or GM-CSF or IL-5 induce dimerization of the respective a chains with $\beta_c$, a phenomenon that leads to receptor activation as measured by tyrosine phosphorylation of $\beta_c$. This is confirmed here, with FIG. 12 showing that in the absence of cytokines antibodies to the α chain (left panel), or $\beta_c$ (right panel), immunoprecipitate their appropriate antigens (α chain and $\beta_c$ respectively). In the presence of IL-3, dimerization of α and $\beta_c$ takes place allowing either anti-α chain or anti $\beta_c$ MoAb to immunoprecipitate both receptor subunits. This is accompanied by tyrosine phosphorylation of $\beta_c$ (top panel). We show in this figure that pre-incubation of the cells with BION-1 blocks receptor dimerizatidn and tyrosine phosphorylation of $\beta_c$. As a control we used the anti $\beta_c$ MoAb 1C1 which was unable to prevent receptor dimerization and activation.

BION-1 Specifically Inhibits Chronic Myelomonocytic Cell Growth

Figure 14:
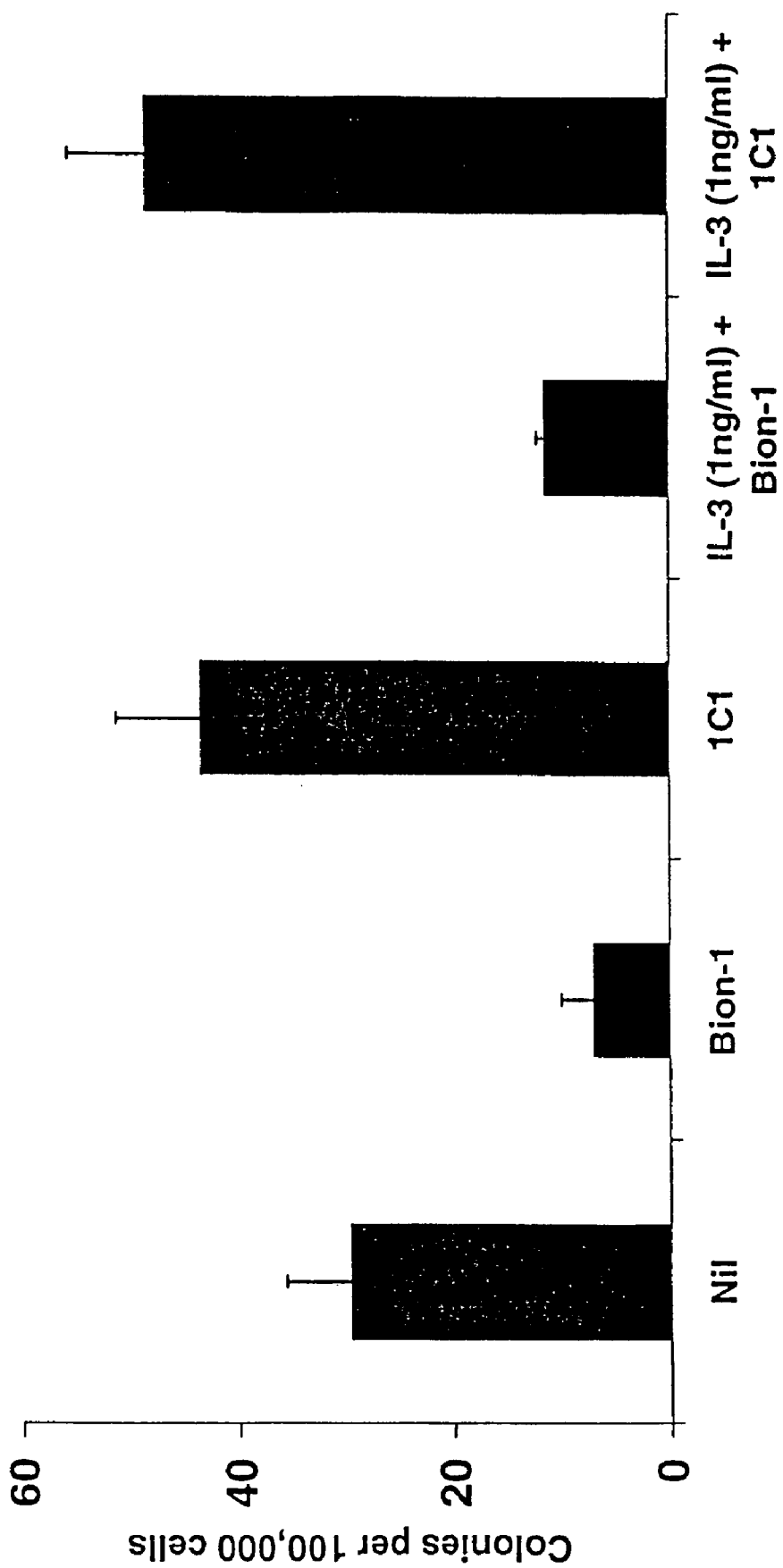
FIG. 14. BION-1 specifically inhibits the growth in vitro of chronic myelomonoctic cells (CMML). A contol antibody (ICI) does not inhibit.

BION-1 is shown to inhibit the activity of one or all of IL-5, IL-3 & GM-CSF mediated effectors of leukaemic cells. In particualr BION-1 inhibits growth in vitro of chronic myelomonocytic cells (CMML), whereas a control antibody (1C1) does not (FIG. 14). Furthermore, BION-1 inhbits even in the presence of IL-3 whereas the control does not.

Screening and Isolation of New Inhibitory Compounds

A large range of potential therapeutic compounds that might act as antagonists, or perhaps agonists of IL-3, GM-CSF and IL-5 individually or collectively, can be readily screened. The screening is initially to determine whether the binding of BION-1 or a fragment thereof to $\beta_c$ receptor or fragment is inhibited. The nature of these inhibitory compounds will not be limited, and the methods used for a binding assay can be any one of the many techniques known to those skilled in the art. Such methods may include affinity selection chromatography, ultrafiltration assays, the scintillation proximity assay, interfacial optical techniques, the quartz crystal microbalance, the jet ring cell, interferometric assays using porous silicon to immobilise the receptor. Reference to such techniques can be found in Woodbury et al 1999, which reference is incorporated herein in its entirety.

Figure 13:
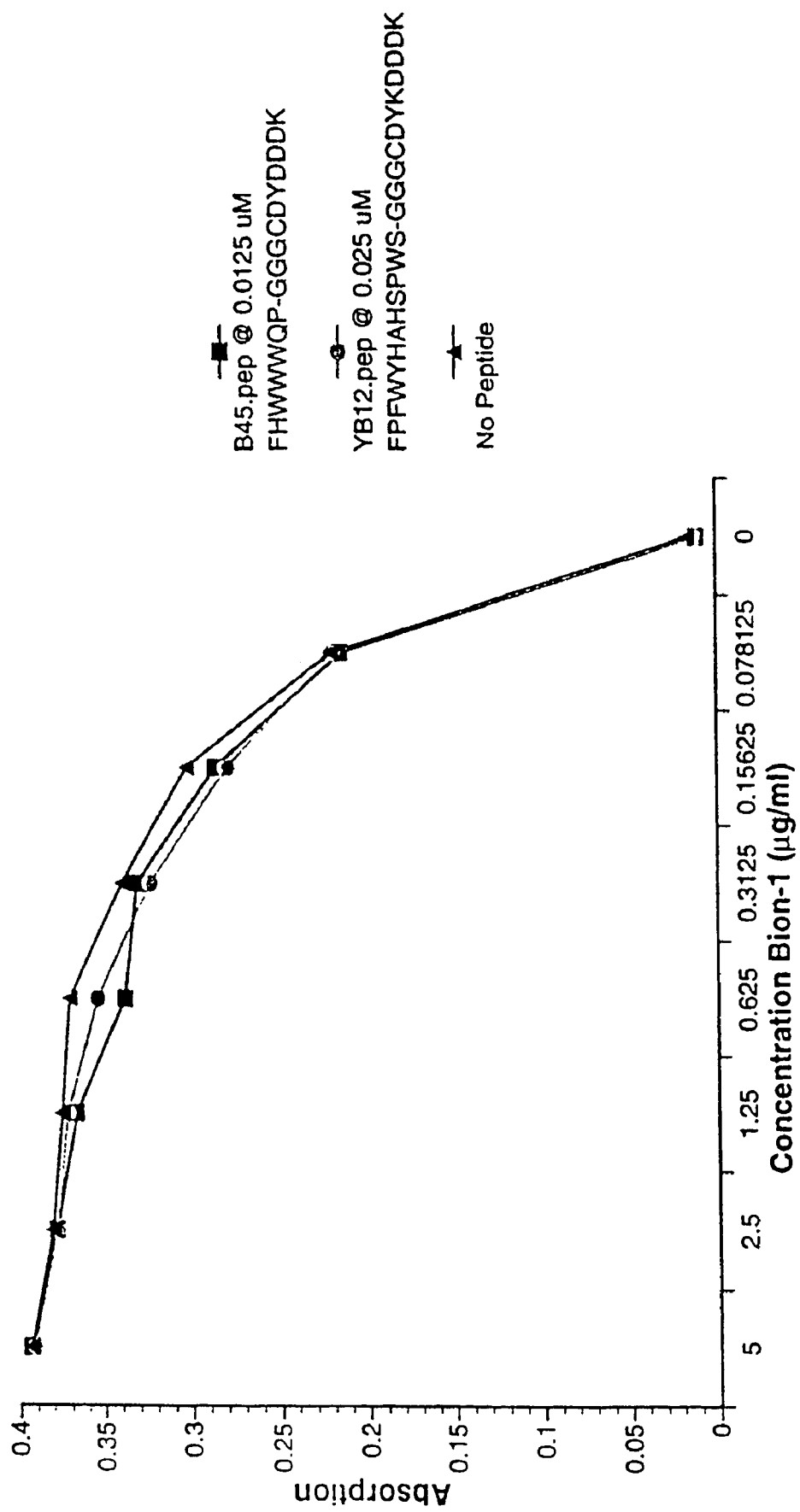
FIG. 13. Screening peptides for inhibition of MoAb BION-1 binding to soluble $\beta_c$ domain 4 adsorbed to solid phase. E. coli derived soluble $\beta_c$ domain 4 (s$\beta_c$#4) was coupled to Maxisorp ELISA plates at 10 µg/1 ml in 0.1M carbonate buffer overnight and then blocked with 1% BSA. (A) B45.pep (FHWWWQP-GGGCDYDDDK) (+) and (B) YB12.pep (FPFWYHAHSPWS-GGGCDYKDDDK) (•) were derived from biopanning libraries with s$\beta_c$#4 using an acid eluant. B45 was allowed the bond to s$\beta_c$#4 at 0.0125 µM and YB12 was allowed to bind s$\beta_c$#4 at 0.025 µM. BION-1 was added to the plates at a starting concentration of 5 µg/ml and serial dilutions were used to titrate the BION-1 down to 0.004 µg/ml. The plate was washed again and BION-1 binding to s$\beta_c$#4 was detected.

The range of therapeutic compounds may include peptides, oligonucleotides, or other small organic or inorganic molecules. FIG. 13 shows the results of screening 7-mer and 12-mer peptide libraries using soluble $\beta_c$ domain 4 supported on ELISA plates.

Deposit of Cell Line

The cell line BION-1 was deposited on the Apr. 29th, 1998 in the American Type Culture Collection (ATCC) at 101801 University Boulevard, Manassas, Va., United States of America and has been designated ATCC HB-12525.

TABLE I

Epitope mapping of Bion-1. Binding affinities of MoAb Bion-1 tested on COS cells transfected with wild type βc or mutants of βc

|  | Bion-1 KD | 1C1 KD |
|---|---|---|
| βc wild type: | 49.3* | 4.4 |
| βc mutated in the B'-C' loop: |  |  |
| M363A/R364A | 0† | 3.8 |
| Y365A | 69.4 | 1.5 |
| E366A | 0 | 2.4 |
| H367A | 27.0 | 2.8 |
| I368A | 21.7 | 2.4 |
| D369A/H370A | 32.4 | 3.6 |
| βc mutated in the F'-G' loop: |  |  |
| R418A | 0 | 1.8 |
| T419A | 23.3 | 3.2 |
| G420A | 53.0 | 1.5 |
| Y421A | 38.9 | 2.3 |

*$K_D$ in nM
0† = not detectable binding

TABLE II

Inhibition of IL-5, GM-CSF and IL-3 mediated eosinophil colony formation by BION-1

|  | [MoAb 8E4] | [MoAb BION-1] (μM) | | | |
|---|---|---|---|---|---|
|  | Medium | (100 μM) | 0.1 | 1 | 10 | 100 |
| IL-5 (1 nM) | 13 ± 4* | 15 ± 3 | 13 ± 4 | 8 ± 2 | 2 ± 2 | 2 ± 0 |
| GM-CSF (2 nM) | 9 ± 4 | 18 ± 4 | 20 ± 4 | 13 ± 4 | 2 ± 2 | 0 ± 0 |
| IL-3 (2 nM) | 4 ± 2 | 8 ± 1 | 8 ± 2 | 4 ± 1 | 1 ± 1 | 0 ± 1 |
| NONE | 0 ± 0 | 0 ± 0 | 0 ± 0 | 0 ± 0 | 2 ± 0 | 0 ± 0 |

*Number of day 14 eosinophil colonies per $10^5$ seeded bone marrow cells. Values shown are the mean from triplicate determination ± SEM.

REFERENCES

Allen et al 1997, *Am J Otolaryngol* 18:239-246
Bagley et al 1997a, *Blood* 89:1471
Bagley et al, 1997b; *J Allergy Clin immunol*; 99;725-728
Barry, S. C., et al (1994) *J. Biol. Chem.*, 269, 8488-8492.
Bates et al, 1996; *J Imunol*, 156:711-718
Contreras, M. A. et al (1983) *Methods Enzymol.*, 92, 277-292.
D'Andrea R J et al, (1996) *Blood* 87:2641-2648
Davis, S. et al (1993) *Science*, 260, 1805-1810.
Fukuda et al 1994, *J Allergy Clin Immunol* 94, 584
Gearing, D. P. et al (1994) *Proc. Natl. Acad. Sci. USA*, 91, 1119-1123.
Giri, J. G., et al (1994) *EMBO J.*, 13, 2822-2830.
Hercus, Blood (1994a) *Blood*, 83:3500
Hercus, T. R. et al (1994b) *Proc. Natl. Acad. Sci. USA*, 91, 5838-5842.
Hibi, M. et al (1990) *Cell*, 63, 1149-1157.
Hilton, D. J. et al (1994) *EMBO J.*, 13, 4765-4775.
Hilton, D. J. et al (1996) *Proc. Natl. Acad. Sci. USA*, 93, 497-501.
Jenkins et al (1995) *EMBO J.* 14:4276
Kimura, Y. et al (1995) *Int. Immunol.*, 7, 115-120.
Korpelainen et al (1993) *Proc Nat. Acad. Sci USA*, 90, 11137-11141
Korpelainen et al (1995) *Blood* 86, 176-182.
Liu, J. et al (1992) *J. Biol. Chem.*, 267, 16763-16766.
Lopez et al, (1990) *Int J Aller gClin Immunol* 85, 99-102
Lopez A F et al (1989). *Proc Natl Acad Sci USA* 86, 7022-7026.
Mauser et al, (1995), *Am J Respir Crit Care Med* 152; 467
McKinnon et al (1997), *J Exp Med* 186:121-129
McConahey et al (1980) *Methods Enzymol* 70:210.
Metcalf; (1986) *Blood* 67:257
Munson, P. J. and Rodbard, D. (1980) *Anal. Biochem.*, 107, 220-239.
Nicoletti, I. et al (1991) *J. Immunol. Methods*, 139:271.
Noguchi, M. et al (1993) *Science*, 262, 1877-1880.
Pennica, D. et al (1995) *J. Biol. Chem.*, 270, 10915-10922.
Russell, S. M. et al (1993) *Science*, 262, 1880-1883.
Scatchard (1949) *Ann N.Y Acad Sci* 51, 660-663
Sun et al (1996) *Blood* 87, 83-92
Sur et al, 1996, J Allergy Clin Immunol 97;1272
Taga, T. et al (1992) *Proc. Natl. Acad. Sci. USA*, 89, 10998-11001.
Takeshita, T. et al (1992) *Science*, 257, 379-382.
Tavernier et al 1995, *Proc Natl Acad Sci USA* 23:5194-5198
Vadas et al (1979) *J Immunol* 122, 1228-1236
Walsh and Crumpton, (1977) *Nature* 269:307.
Woodbury, C. P. et al (1999) *J Chromatogr B Biomed Sci Appl* 725(1):113-37.
Woodcock et al (1994) *EMBO J* 13:5176
Woodcock et al, (1996) *J Biol Chem* 271, 25999-26006
Zurawski, S. M. et al (1993) *EMBO J.*, 12, 2663-2670.

The invention claimed is:

1. A method of inhibiting IL-5, IL-3 or GM-CSF mediated proliferation of a chronic myelomonocytic cell by contacting said cell with a monoclonal antibody BION-1 or a fragment thereof capable of inhibiting binding of cytokines IL-3, GM-CSF or IL-5 to the common receptor βc, wherein the monoclonal antibody or fragment thereof binds to both the B'-C' loop and the F'-G' of domain 4 of the βc subunit, wherein said contacting results in inhibition of IL-5, IL-3 or GM-CSF mediated proliferation of said cell.

2. A method of inhibiting IL-5, IL-3 or GM-CSF mediated eosinophil activation, eosinophil production or eosinophil survival, by contacting an eosinophil with a monoclonal antibody BION-1 or a fragment thereof capable of inhibiting the binding of cytokines IL-3, GM-CSF or IL-5 to the common receptor βc, wherein the monoclonal antibody or fragment thereof binds to both the B'-C' loop and the F'-G' of domain 4 of the βc subunit, wherein said contacting results in inhibition of IL-5, IL-3 or GM-CSF mediated activation, production or survival of said eosinophil.

* * * * *

UNITED STATES PATENT AND TRADEMARK OFFICE
CERTIFICATE OF CORRECTION

| | | |
|---|---|---|
| PATENT NO. | : 7,427,401 B2 | Page 1 of 1 |
| APPLICATION NO. | : 10/774887 | |
| DATED | : September 23, 2008 | |
| INVENTOR(S) | : Lopez et al. | |

It is certified that error appears in the above-identified patent and that said Letters Patent is hereby corrected as shown below:

On the Title page,

[*] Notice: Subject to any disclaimer, the term of this patent is extended or adjusted under 35 U.S.C. 154(b) by 191 days Delete the phrase "by 191 days" and insert -- by 459 days --

Signed and Sealed this

Fourth Day of May, 2010

David J. Kappos
*Director of the United States Patent and Trademark Office*